US008645166B2

(12) United States Patent
Bessette

(10) Patent No.: US 8,645,166 B2
(45) Date of Patent: Feb. 4, 2014

(54) SYSTEM AND METHOD FOR SCORING ILLNESS COMPLEXITY TO PREDICT HEALTHCARE COST

(75) Inventor: Russell W. Bessette, Prospect, KY (US)

(73) Assignee: Russell W. Bessette, Prospect, KY (US)

( * ) Notice: Subject to any disclaimer, the term of this patent is extended or adjusted under 35 U.S.C. 154(b) by 0 days.

(21) Appl. No.: 13/487,112

(22) Filed: Jun. 1, 2012

(65) Prior Publication Data

US 2012/0303381 A1  Nov. 29, 2012

Related U.S. Application Data

(63) Continuation-in-part of application No. 11/903,846, filed on Sep. 25, 2007, now Pat. No. 8,219,414.

(60) Provisional application No. 61/522,761, filed on Aug. 12, 2011, provisional application No. 61/493,037, filed on Jun. 3, 2011, provisional application No. 61/492,407, filed on Jun. 2, 2011, provisional application No. 60/959,670, filed on Jul. 16, 2007.

(51) Int. Cl.
*G06Q 50/00* (2012.01)
*G06Q 10/00* (2012.01)

(52) U.S. Cl.
USPC .................................................. 705/3; 705/2

(58) Field of Classification Search
USPC ............................................................ 705/3
See application file for complete search history.

(56) References Cited

U.S. PATENT DOCUMENTS

| 8,219,414 | B2 * | 7/2012 | Bessette et al. | 705/2 |
|---|---|---|---|---|
| 2002/0111826 | A1 * | 8/2002 | Potter et al. | 705/2 |
| 2003/0212579 | A1 * | 11/2003 | Brown et al. | 705/2 |
| 2005/0033678 | A1 | 2/2005 | Huneault | |
| 2005/0234742 | A1 | 10/2005 | Hodgdon | |
| 2005/0256745 | A1 | 11/2005 | Dalton | |
| 2010/0076787 | A1 | 3/2010 | Naylor et al. | |
| 2010/0311482 | A1 | 12/2010 | Lange | |
| 2011/0052488 | A1 | 3/2011 | Dennis et al. | |

OTHER PUBLICATIONS

Berlin, A comparison of statistical methods for combining event rates from clinical trials, 1989, Statist. Med., 8: 141-151. doi: 10.1002/sim.4780080202.*
Berlin, A comparison of statistical methods for combining event rates from clinical trials, 1989, Statist. Med., 8:141-151. doi: 10.1002/sim.4780080202.*
International Search Report mailed Aug. 22, 2012 which issued in corresponding to International Patent Application No. PCT/US2012/40592 (4 pages).
Written Opinion mailed Mar. 2, 2009 Aug. 22, 2012 which issued in corresponding to International Patent Application No. PCT/US2012/40592 (6 pages).

* cited by examiner

*Primary Examiner* — Tran Nguyen
(74) *Attorney, Agent, or Firm* — Middleton Reutlinger; John F. Salazar

(57) ABSTRACT

A processor-based method for presenting patient test data includes acts of obtaining values of factors indicative of different patient health parameters and operatively associating the values of the factors with a unique identifier in a database borne by a physical computer-readable medium. Using a processor, a Z-score is determined for each factor and absolute values for each Z-score are converted into logarithm values. On a display, a radar graph depicts the Z-scores for the plurality of factors, the radar graph defining at least an arc subdivided into a plurality of sectors, each sector being subdivided into a plurality of arcuate sections, wherein log values are plotted from a center point of the radar graph, with the Z-scores of identified ones of the plurality of factors being representing as highlighted arcuate sections extending from the center point of the radar graph outwardly in correspondence with a magnitude of each Z-score.

15 Claims, 14 Drawing Sheets

Total ICS:126.0783

Total ICS:226.2969

FIG. 4

|  | Variable Coefficient | p-value |
|---|---|---|
| Constant | -2.84 |  |
| Age | 0.01 | 0.10 |
| Stage CKD | 1.24 | 0.03 |
| PO4 | 0.15 | 0.04 |
| PTH | 0.00 | 0.33 |
| Glu | 0.01 | 0.57 |
| Hgb | -0.33 | 0.00 |
| NCO3 | -0.03 | 0.71 |
| Albumin | -0.28 | 0.00 |
| Creat | 0.03 | 0.01 |
| BUN | 0.01 | 0.55 |
| Potassium | -0.07 | 0.33 |
| Calcium | 0.08 | 0.25 |
| Sodium | 0.06 | 0.53 |
| Alk-P | -0.01 | 0.92 |
| ALT | 0.31 | 0.00 |
| WBC | 0.17 | 0.00 |
| eGFR | 0.08 | 0.00 |

|  | Variable Coefficient | p-value |
|---|---|---|
| Constant | -2.84 |  |
| Age | 0.01 | 0.09 |
| Stage CKD | 1.31 | 0.02 |
| PO4 | 0.17 | 0.01 |
| Hgb | -0.31 | 0.00 |
| Albumin | -0.25 | 0.00 |
| Creat | 0.03 | 0.00 |
| ALT | 0.30 | 0.00 |
| WBC | 0.16 | 0.00 |
| eGFR | 0.08 | 0.00 |

FIG. 5

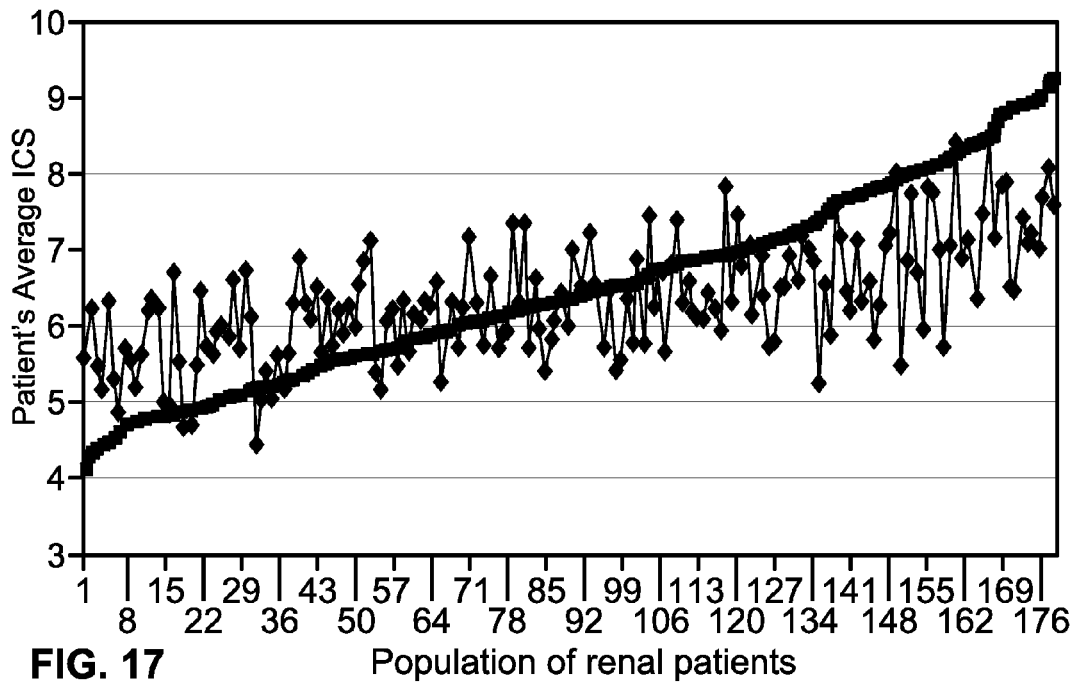
FIG. 17  Population of renal patients
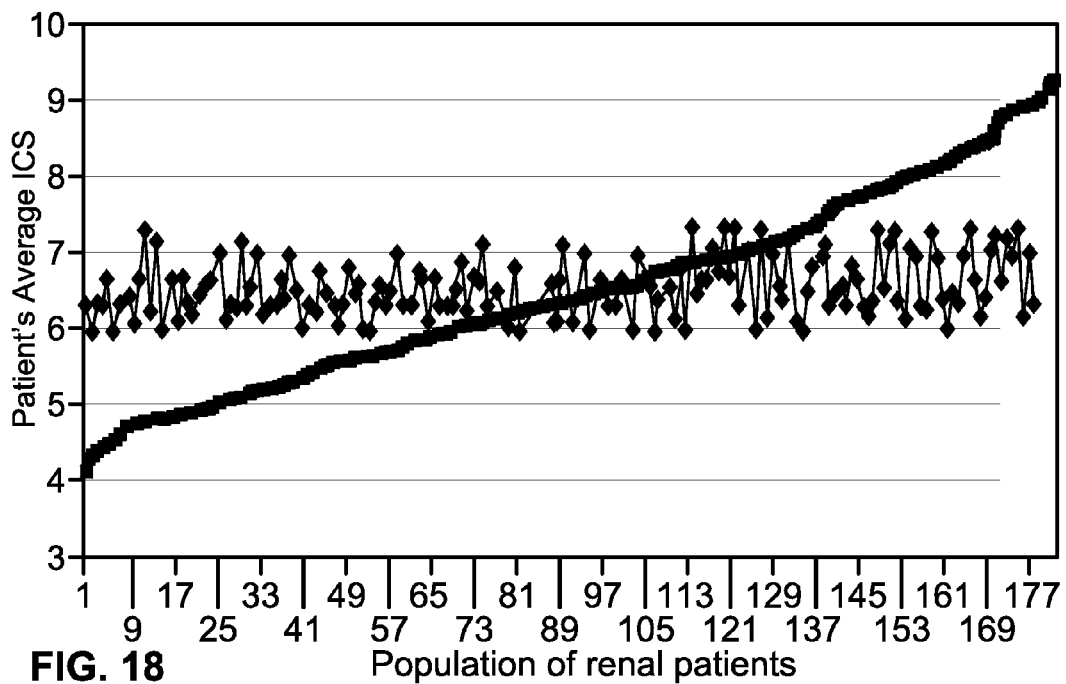
FIG. 18  Population of renal patients

SYSTEM AND METHOD FOR SCORING ILLNESS COMPLEXITY TO PREDICT HEALTHCARE COST

CLAIM TO PRIORITY

The present non-provisional patent application claims the benefit of priority to U.S. Provisional Patent Application Ser. No. 61/492,407, filed Jun. 2, 2011, U.S. Provisional Patent Application Ser. No. 61/493,037, filed Jun. 3, 2011, and U.S. Provisional Patent Application Ser. No. 61/522,761, filed Aug. 12, 2011, each of which is hereby incorporated by reference in its entirety, and further claims the benefit of priority to U.S. patent application Ser. No. 11/903,846, filed Sep. 25, 2007, from which the present non-provisional patent application is a continuation-in-part application, and from U.S. Provisional Patent Application Ser. No. 60/959,670, filed Jul. 16, 2007, each of which is hereby incorporated by reference in its entirety.

COPYRIGHT

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

The present invention relates generally to healthcare costs and relates more particularly to a system and method for scoring illness complexity to predict healthcare cost.

BACKGROUND OF THE INVENTION

Despite significant federal and state investments to transition patient medical records to all-electronic systems, and a generalized expectation of policy makers that quality of healthcare could someday be precisely defined and measured, a definitive correlation between healthcare quality and cost has remained out of reach. Petersen et al. in an extensive review of the literature compared various methods to improve quality through pay-for-performance programs. (Petersen L, Woodard L, Urech T, et al.: Does pay-for-performance improve the quality of health care? Ann Intern Med 145:265-272 2006). Their analysis concluded that most financial incentives were focused on the delivery of prevention services rather than health outcomes. Other investigators reported that so-called pay-for-performance programs impact some patients negatively, particularly those with mental illness and chemical dependency. (Shen Y: Selection incentives in a performance-based contracting system. Health Serv. Res. 38:535-552 2003; Norton E: Incentive regulation of nursing homes. J. Health Econ. 11:105-128 1992; Rosenthal M, Frank R, Li Z, et al: Early experience with pay-for-performance: from concept to practice. JAMA. 294:1788-1793 2005). Such analyses reveal that American healthcare competes on delivery of the lowest procedure price rather than a value-based outcome for individual patients. (Porter M, Teisberg E: Redefining Healthcare. Harvard Business Press, ISBN 1-59139-778-2, 2006; Baker L: Measuring competition in health care markets. Health Serv. Res. 36: 223-251, 2001; Scanlon D, Swaminathan S, Lee W, et al.: Does competition improve health care quality? Health Serv. Res. 43: 1931-1951 2008.)

In order to measure treatment outcomes and compensate providers fairly, improved measuring tools are necessary. Currently, most payers score quality care based on delivery of services focused in prevention such as up-to-date immunizations, early diagnostic studies such as mammography, colonoscopy, PAP smears, PSA testing, or education in healthy life styles. (Landon B, Zaslaysky A, Beaulieu J, et al.: Health plan characteristics and consumer's assessments of quality. Health Affairs 20: 274-286, 2001; Scanlon D, Darby C, Rolph E, et al.: The role of performance measures for improving quality in managed care organizations. Health Sery Res. 36: 619-641, 2001.) Though these services are valuable, patients still develop chronic illnesses that require treatment or palliative care. Indeed, treatment for such chronic conditions represents a large portion of healthcare budgets. In order to grade treatment outcomes fairly, each patient should be scored as to their level of illness complexity prior to the start of treatment, so that outcomes are judged among patients of similar severity.

Currently, disease "staging" is a prime method for relating disease severity to reimbursement levels. Chronic kidney disease ("CKD") typifies such a condition with five stages of severity based on a declining glomerular filtration rate. However, many of these patients are at risk for higher complexity due to co-morbid factors like hypertension, diabetes, and congestive heart failure. CKD is often associated with multiple organ dysfunctions that impact cost, health, and work productivity, the diversity of treatment modalities required to care for these patients may lead to disagreements between providers and payers on therapy approval and reimbursement. Unfortunately, payers may have incomplete information about the severity of these co-existing morbidities, and therefore must rely primarily on a general CKD staging to evaluate quality care. Payment by stage of illness also provides a convenient method to aggregate cost and grade treatment upon the overall public health. (Johnson C, Levey A, Coresh J, el al.: Clinical practice guidelines for chronic kidney disease in adults: Part 1. Definition, disease stages, evaluation, treatment, and risk factors. American Family Physician 70: 869-876, 2004; Smith D, Gullion C, Nichols G, et al.: Cost of medical care for chronic kidney disease and comorbidity among enrollees in a large HMO population. J. Amer Soc Nephrology 15: 1300-1306, 2004.)

Unfortunately, clinical experience suggests that these ordinal measures for renal disease, along with other diseases, though ideal for population reports, do not fully account for illness complexity seen in individual patients. When pay-for-performance is linked to grading of illness by stage, it may imply quality on a population basis, however, if the true level of illness complexity at the start of treatment is unknown, then the value of any outcome compared to the cost in achieving it, also remains unknown. (Born P, Simon C.: Patients and profits: the relationship between HMO financial performance and quality of care. Health Affairs 20: 167-174, 2001; Kessler D, Geppert J.: The effects of competition on variation in the quality and cost of medical care. Jour of Economics and Management Strategy 14: 575-589, 2005; McGlynn E, Asch S, Adams J, et al.: The quality of health care delivered to adults in the United States. New England Journal of Medicine 348: 2635-2645, 2003.)

With the introduction of Accountable Care Organizations ("ACO") in the United States, there is a new focus on provider compensation. Under this system, providers are encouraged to enter into risk adjusted capitation agreements within a patient-centered medical home. Under this system, determining risk on small patient groups could prove difficult and compel both payers and providers to accept reimbursement based on population averages not reflecting unique features within given population groups, such as population groups of different ethnicity or of different locality.

Healthcare providers and consumers are both investigating ways to reduce costs in providing healthcare services and treatment, while still maintaining or improving patient outcomes. Some metrics are used to track the performance of healthcare providers, but most quality assurance systems use claims to infer population outcomes. Numerous quality metrics currently exist but nearly all are based on claims data analysis, which relates the number and cost for specific treatment procedures (CPT Codes) to individual diagnostic codes (ICD-9, ICD-10) for patient illness. All of the currently existing quality metrics use quality measures based on tabulation of preventative measures deployed within a population, which fail to provide a patient and provider specific analysis.

SUMMARY OF THE INVENTION

The present concepts identify a need for a system and method for generating an illness complexity score relating blood chemistry values to reimbursement values and disclose systems and methods for generating an illness complexity score relating blood chemistry values to reimbursement values to thereby address such identified need. The present concepts more particularly present methods and systems to relate healthcare cost/charges to individual patients and providers based on illness complexity and provider treatment choices, thus providing value-based outcome measurements for risk adjusted payment. The methods and systems presented herein provide, finally, means to realize value-based outcomes for medical treatment and, thereby, means to optimize medical results in relation to healthcare cost.

The present concepts further relate to methods and systems to relate illness severity within primary disease groups to prediction of treatment cost.

Since at least some aspects of the methods and systems disclosed herein are based on personalized blood and physical test results, routinely collected as part of a general medical examination, additional benefits are realized at no additional testing or laboratory cost.

Yet further, computerized analysis of large datasets in accord with at least some aspects of the present concepts permits near real-time classification of healthcare results over dynamic ranges of time. In this manner, both payers and patients can monitor illness progression, compare preferred treatment methods, intercept complications, and classify value-based treatment outcomes.

According to one aspect of the present invention, a processor-based method for presenting patient test data on a display device includes the steps of obtaining values of a plurality of factors indicative of different patient health parameters, the plurality of factors comprising at least a plurality of blood chemistry test results, and operatively associating the values of the plurality of factors with a unique identifier for the patient in a database borne by at least one physical computer-readable medium. The processor-based method further includes the steps of determining a Z-score for each of the plurality of factors using at least one processing device and converting absolute values for each Z-score into logarithm values using the at least one processing device. The processor-based method further includes the step of plotting or otherwise displaying, on the display device or on a printing device, a radar graph depicting the Z-scores for the plurality of factors, the radar graph defining at least an arc subdivided into a plurality of sectors, each sector being subdivided into a plurality of arcuate sections, wherein log values are plotted from a center point of the radar graph, with the Z-scores of identified ones of the plurality of factors being representing as highlighted arcuate sections extending from the center point of the radar graph outwardly in correspondence with a magnitude of each Z-score.

According to another aspect of the invention, a system for displaying patient test data on a display device includes a computer comprising a display device, at least one input device, at least one processor and a communication device and at least one local or remote physical computer-readable medium storing instructions that, when executed by the at least one processor or another processor, cause the system to obtain from a database borne by at least one physical computer-readable medium values of a plurality of factors indicative of different patient health parameters, the plurality of factors comprising at least a plurality of blood chemistry test results and to determine a Z-score for each of the plurality of factors using at least one processing device. The at least one local or remote physical computer-readable medium further stores instructions that, when executed by the at least one processor or another processor, cause the system to convert absolute values for each Z-score into logarithm values using the at least one processing device and to display, on the display device, a radar graph depicting the Z-scores for the plurality of factors, the radar graph defining at least an arc subdivided into a plurality of sectors, each sector being subdivided into a plurality of arcuate sections, wherein log values are plotted from a center point of the radar graph, with the Z-scores of identified ones of the plurality of factors being representing as highlighted arcuate sections extending from the center point of the radar graph outwardly in correspondence with a magnitude of each Z-score.

According to yet another aspect of the invention, a processor-based method for determining an illness complexity score includes the acts of obtaining values of a plurality of factors indicative of different patient health parameters, the plurality of factors comprising at least a plurality of blood chemistry test results, storing the values for the plurality of factors in a database borne by a physical computer-readable medium, and using a processing device, performing a linear regression calculation for each of the plurality of factors to determine a Beta coefficient and a p-value for each of the plurality of factors. The processor-based method for determining an illness complexity score also includes the acts of using the processing device, performing a backward selection process on the results of the linear regression calculations to identify results demonstrating a correlation with cost above a predetermined threshold, storing the Beta coefficients, p-values and linear regression constants in the database of the physical computer-readable medium, in a different database of the physical computer-readable medium, or in another database of another physical computer-readable medium, and displaying on a display device, or printing on a printing device, selected ones of the plurality of factors having at least one of Beta coefficients, p-values or linear regression constants above a threshold value.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 4 shows a table for full test variables before performing a step-wise parsimonious regression calculation in accord with at least some aspects of the present concepts FIG. 5 shows a test table after a step-wise parsimonious regression calculation of the test variables of FIG. 4 showing those values demonstrating the greatest correlation with cost in accord with at least some aspects of the present concepts.

FIG. 17 is an exemplary line graph for a population of renal patients (x-axis) depicting each patient's average ICS (y-axis) along with each patient's respective natural logarithm for average monthly reimbursement in accord with at least some aspects of the present concepts.

FIG. 18 is an exemplary line graph for a population of renal patients (x-axis) with an average CKD stage that ended worse than their starting stage in accord with at least some aspects of the present concepts.

Figure 1:
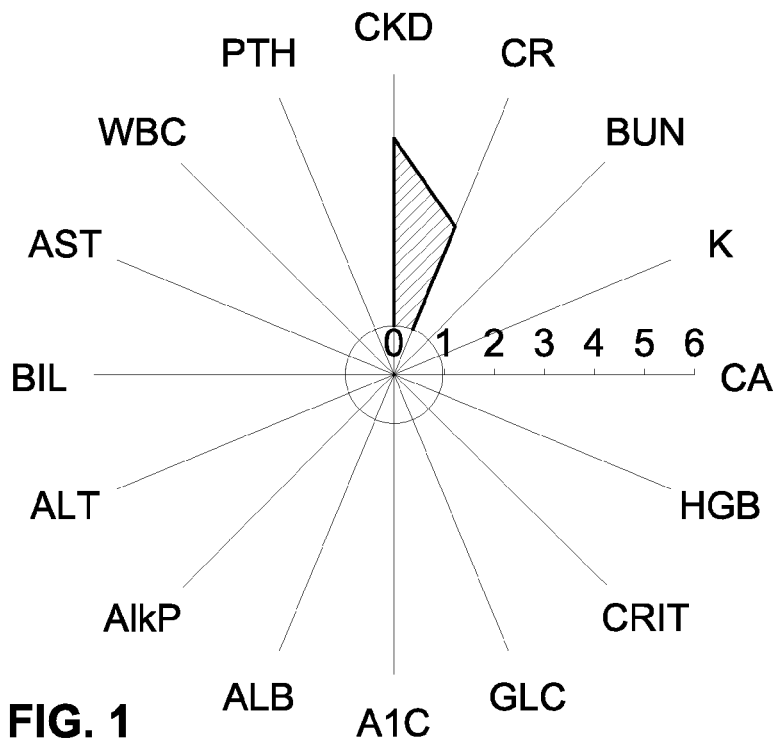
FIG. 1 is a graph demonstrating, in accord with at least some aspects of the present concepts, a severity of a patient's disease at a certain stage.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

The present invention may be embodied as a method for determining an Illness Complexity Score ("ICS") formula for a particular illness (disease). Illness or disease is defined as a condition of a living animal or plant that impairs normal functioning and is recognized by distinguishing signs and symptoms. These distinguishing signs and symptoms are confirmed by objective measurements or tests, which may include among others, blood chemistry values, physiologic function studies, genetic profiles, and diagnostic imaging.

When any test value deviates from its normal range, (that is: the range generally observed in a healthy population), then that test value alone, or as part of a group of associated test values, confirms a specific disease or illness. The degree by which a test value deviates from its normal range is significant—the greater the deviation away from normal, (above or below normal) the greater the severity of disease.

If the total pool for all diagnostic Tests (T) known to the healthcare profession are represented by $T_{1...n}$, and if all Diseases (D) known to the healthcare profession are represented by $D_{1...n}$, then any specific Disease (D) and its confirming Tests can be represented as $D_{1...n} = TX_{1...n}$ where $X_{1...n}$ represents those specific tests required to confirm a specific Disease within the array $D_{1...n}$.

If the total pool for all diagnostic Tests (T) known to the healthcare profession are represented by $T_x$, and if all Diseases (D) known to the healthcare profession are represented by $D_n$, then any specific Disease and its confirming Tests can be represented as $D=T_x$ or $D_n=T_x$ where $x_n$ represents the number of specific tests required to confirm a specific Disease within the array $D_n$.

Some individuals can have more than one disease simultaneously. This condition is referred to as co-morbidity. Certain illnesses commonly occur together, for example, Chronic Kidney Disease ("CKD") has both diabetes and congestive heart failure ("CHF") occurring with it routinely. The representation of multiple diseases and their required confirming tests could be represented by:

$$D_1 = (T_{X1...n}) + D_2 = (T_{Y1...n}) + D_3 = (T_{Z1...n}), \quad \text{(Eq. 1)}$$

$$D_1 + D_2 + D_3 = T_{x_1} + T_{x_2} + T_{x_3} \quad \text{(Eq. 2)}$$

where $D_1$ might stand for CKD, $D_2$ might stand for Diabetes, $D_3$ might stand for CHF. The specific confirming tests necessary to confirm each of those diseases are represented by: $T_{x_1}$, $T_{x_2}$, and $T_{x_3}$, respectively. The confirming tests for any disease are chosen from peer reviewed literature and may change or grow over time (e.g., to include genetic testing) and any new tests can be added to the overall array.

Healthcare payers require patient specific information, as opposed to population averages, in order to score illness severity, predict likely hospital admission, and risk-adjust payment to providers while at the same time assuring ideal public health. The present methods and systems employ "Q" (Quality) scoring to dynamically score illness severity and compare treatment results over time to cost. The present methods and systems provide tools to relate healthcare cost/ charges to individual patients and providers based on each patient's illness complexity and provider treatment choices, thus providing value-based outcome measurements for risk adjusted payment. The present methods and systems are, moreover, patient/provider specific and are not based on inferred population averages, but are rather based on objective, physician chosen data that provides dynamic, real-time measures of health response to treatment and its cost.

Currently most insurance payers and hospital providers employ HEDIS scores (Healthcare Effectiveness Data and Information Set), ordinal stages of disease, single blood markers (e.g. A1c, Hgb), and population claims data to evaluate quality of healthcare delivery. HEDIS scores are a widely used set of performance measures in the managed care industry, developed and maintained by the National Committee for Quality Assurance (NCQA). However, though these measures are ideal for measuring preventive care, none of these factors are connected to scoring individual patient illness complexity, treatment outcome, or cost.

The first premise underlying the present methods and systems is that healthcare costs rise with increasing illness severity.

The second premise underlying the present methods and systems is that healthcare outcomes can be compared by measuring the change in illness severity over treatment time and dividing that result by the cost to achieve it. This may be expressed as the ROI (Return on Investment) which is equal to the health outcome over the time to achieve it divided by cost, where the health outcome is equal to the change in each patient's illness severity score over treatment time. Thus, expressed in the form of an equation:

$$\text{ROI} = ((\text{Starting ICS} - \text{Ending ICS})/\text{Treatment Time})/\text{Cost} \quad \text{(Eq. 3)}$$

where cost is measured as the natural logarithm of total expended dollars to achieve the outcome (e.g., ln. average monthly cost for treatment time in months).

Although humans, as any organism, may be afflicted with one primary illness, it's also common for multiple illnesses to infect a single individual. Illnesses that exist with a primary disease are called co-morbid conditions. Their occurrence can significantly impact disease severity and progression as well as higher cost of care. The methods and systems described herein recognize that accurate measurement of patient outcome should consider factors (e.g., score for illness severity; score for treatment outcome, cost over time to achieve an outcome, etc.) presently overlooked in conventional quality measures for efficiently and effectively providing patient healthcare services. A key deficiency in the conventional quality measures is the failure to quantify the influence of common co-morbid conditions on the outcome and progression of a primary disease.

Whether by private or public insurance, current methods pay for healthcare based on identification of a primary illness, as classified within the International Classification of Diseases (ICD-9), and then match that diagnosis to expected treatment procedures that are computer coded and contained within the Current Procedure Terminology (CPT) code dictionary. Insurance payers then evaluate appropriate reimbursement for care based on the expected average fee for physicians located within the geographic zone of the ill patient. Patients with multiple co-morbid conditions may have a higher degree of illness complexity than patients with only a single ICD-9 illness. For example, two patients may both have the same classification of gall bladder disease, but one of them may be complicated by senility, obesity, diabetes, hypertension and hereditary anemia. That patient has a greater risk for delayed healing and treatment complications and may require more treatment resources than a younger healthier individual.

Classifying a pool of patients by their primary diagnosis can lead payers to assume both patients are similar even though, as noted above, the co-morbidity presents different illness complexity. In addition, since there is no scalar scale to classify treatment results over time, treatment outcomes cannot be judged objectively. Patients requiring more resources to manage higher illness complexity may thus encounter delayed insurance approval for treatment, or may trigger classification of their physician as an outlier. Without an objective measurement of illness severity at the start of treatment, and a similar measurement upon completion, a value-based assessment of health outcome becomes pure conjecture.

Previous methods are available to measure illness complexity/severity, as disclosed in the present inventor's own U.S. patent application Ser. No. 11/903,846, which is hereby incorporated by reference in its entirety. The methods and systems disclosed herein consider the values produced from the illness severity/complexity measurement method disclosed in the present inventor's U.S. patent application Ser. No. 11/903,846 to measure healthcare outcomes.

In order to report a final ROI, the presently disclosed methods and systems require collection of data, and transforming of the data it into one or more data structure(s) and database(s) that permit calculation of individual illness complexity scores over time and relating such changes to cost. With this organized data, the presently disclosed methods and systems permit illness modeling to predict future treatment possibilities and outcomes personalized to individual patients. Further, the presently disclosed methods and systems enhance patient compliance with treatment by providing information displayed to patients, providers and payers in a manner that facilitates enhanced understanding.

Figure 2:
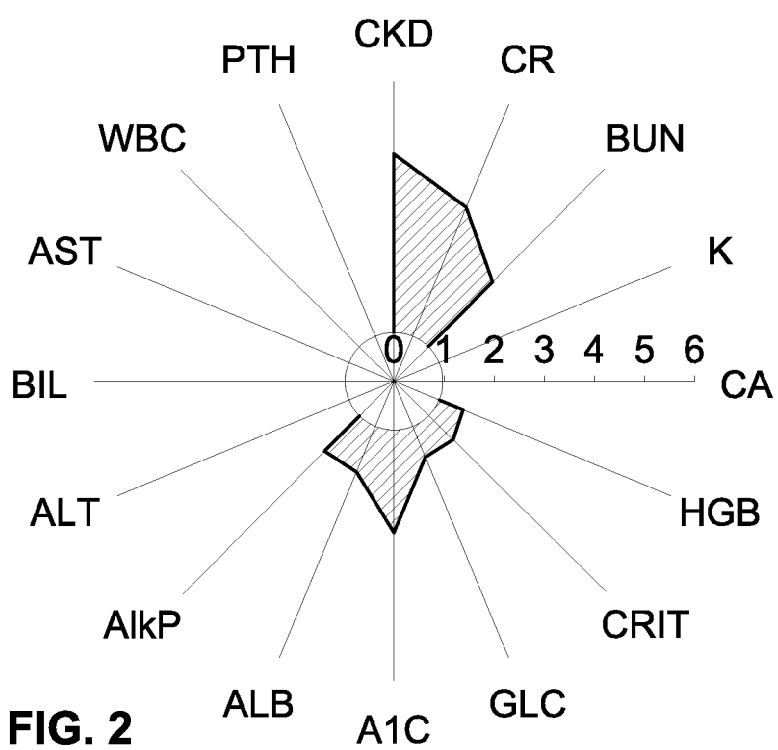
FIG. 2 is a graph demonstrating, in accord with at least some aspects of the present concepts, a severity of a patient's disease at a certain stage.

FIG. 1 is a graphical representation of a severity of a patient's disease at a specified stage produced using the methods of the inventor's U.S. patent application Ser. No. 11/903, 846. FIG. 2 is, likewise, a graphical representation of a severity of a different patient's disease at the same specified stage as that of FIG. 1, also produced using the methods of the inventor's U.S. patent application Ser. No. 11/903,846. As can be seen in FIG. 2, there are not only indications at CKD/ CR, but also at CR/BUN and further at AlkP/ALB/A1C/GLC/ CRIT/HGB. FIGS. 1-2 demonstrate that two different patients at the same stage can have different severity levels, which is significant in properly assessing healthcare outcomes.

Figure 3:
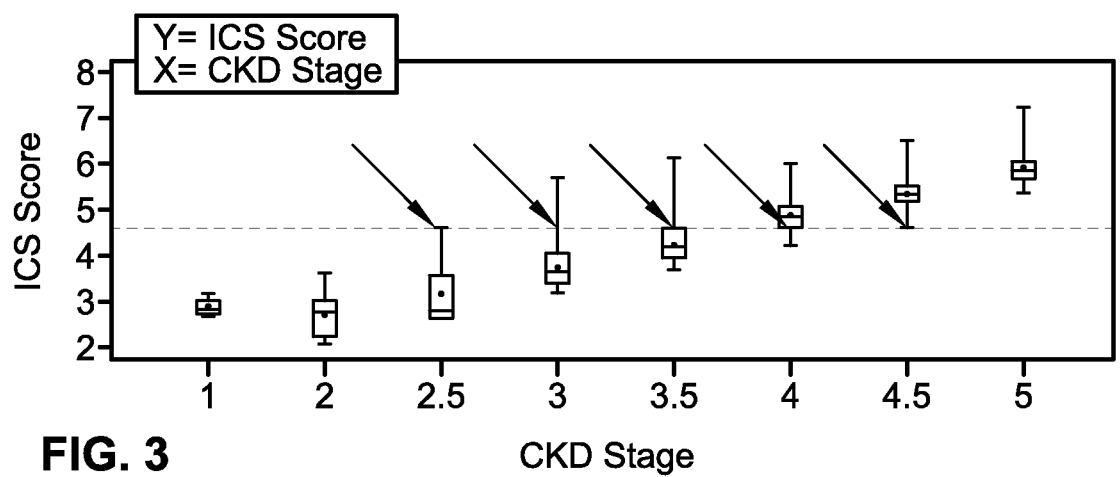
FIG. 3 is a graph demonstrating, in accord with at least some aspects of the present concepts, that one ICS score can signify the severity level across each stage of a disease.

FIG. 3 shows a box and whisker plot of about de-identified 1100 chronic kidney disease (CKD) patients studied over one year, with the x-axis representing the last chronic kidney disease (CKD) stage (i.e., the ending CKD stage for the patients) from 1 (mild) to 5 (severe), and the y-axis representing the last or ending Illness Complexity Score (ICS). The ICS methodology is premised, at least in part, on deviation of serum chemistry values from a normal range and such deviations can be utilized separately or in combination with any number of other types of objective measurements or tests considered diagnostic for each disease such as, but not limited to, physical measurements (e.g., height, weight, percent body fat, tumor size, etc.) physiologic measures (e.g., cardiac stress tests, genetic profiles, etc.), or diagnostic imaging (e.g., x-rays, MRI's, etc.). Each diagnostic test has, by convention, an expected normal range (i.e., the range of values observed in a statistically significant population of healthy people (e.g., 96%)). When a test value is outside that normal range, however defined, it suggests illness and along with other abnormal test results will confirm the diagnosis for a specific disease or illness. The degree by which a test value deviates from its normal range also suggests the severity and/or progression of an illness or disease.

For the above-noted population of de-identified patients, patients without a calculated stage of kidney disease or a repeated eGFR that was at or below 60 ml/min over a three-month period were excluded (216 patients), since they may have represented acute renal disease, which was not the focus of this study. After exclusion, 888 CKD patients remained in the sample. A total of eighteen blood tests were requested from the MCO for analysis by a consulting group of university nephrologists. The choice of tests was made based on each variable's perceived importance in monitoring the health of CKD patients. The 18 blood tests were: serum phosphorus, parathyroid hormone ("PTH"), glucose, glycolated hemoglobin ("HbA1c"), hemoglobin, bicarbonate, albumin, creatinine, blood urea nitrogen ("BUN"), potassium, calcium, sodium, alkaline phosphatase, alanine aminotransferase ("ALT"), bilirubin, leukocytes, and eGFR. The data set also included the complete financial profile for all medical claims that were paid for services for these patients over the same time period. These costs were also studied.

Since blood tests ordered by physicians showed marked variation in selection and repetition, we filtered the remaining pool of 888 patients into a data set of 177 patients with no missing values for the following fifteen tests that were repeated at least twice or more over the study period: phosphorus, PTH, glucose, hemoglobin, bicarbonate, albumin, creatinine, urea nitrogen, potassium, calcium, sodium, alkaline phosphatase, ALT, WBC (leukocytes), and eGFR. The blood tests for all patients at all times were performed by the same laboratory. Thus, the units of measurement and normal range for each test were common to all observations.

Data for each patient was organized on a spreadsheet with columns labeled for patient ID, date of medical service, payments for all reimbursed medical care, CKD stage, and results of each blood test. Rows were grouped by patient ID and chronological dates for medical services. Since all fifteen blood tests were not repeated on each date that a medical procedure was delivered, test results were carried forward to subsequent rows until replaced by a fresh test result. The average number of data rows for each patient was 13.1 with most patients having one or more tests repeated in 8 of the 13 study period months.

In FIG. 3, the Y-axis displays the natural logarithm of the weighted values for a calculated ICS. Within the box range are contained the ICS score values for approximately ⅔ of the patients classified at a given stage (1-5). The whiskers contain the score values for ⅓ of the patients at a given stage of CKD. The horizontal line within each box is the average score for all patients with a given stage of CKD. As can be seen across any horizontal line from the Y-axis, patients in a lower stage of CKD can have illness complexity scores associated with higher stages of CKD. For example, a patient classified as a Stage 3, (mild CKD) could have a degree of illness severity as great as a Stage 5 patient. Thus, FIG. 3 illustrates that one ICS score can individually represent a severity level of illness across a plurality of stages of, and possibly all of the stages of, the disease.

In accord with at least some aspects of the present concepts, the aforementioned collection of patient data and transforming of the patient data it into one or more data structure(s) and database(s) that permit calculation of individual illness complexity scores over time and relating such changes to cost includes the collection over time of and/or submission over time of, for example, routine blood chemistry test results (e.g., as ordered by each patient's physician), routine physical measures (e.g., blood pressure, BMI, waist circumference, etc.) collected as part of each patient's regular physical examination or are added to the data file by each patient, and/or blood chemistry values obtained from physician EMR records or, preferably, by direct laboratory feed.

In one embodiment, such patient data, once obtained, is transformed for display on a display device or printing device in a manner (e.g., on spreadsheets) such that the data is operatively associated with a unique identifier for each patient's results (e.g., a first column of cells in a spreadsheet contains a unique identifier for each patient's results). Continuing with such embodiment, the data is further presented in association with (e.g., in subsequent adjacent columns of a spreadsheet) information on patient demographics, age, gender, specific blood chemistry test results, and physical measurements, ICD-9 codes for each primary diagnosis, CPT procedure codes, and dollar amounts for all healthcare services rendered. The latter three data values are collected from each patient's payer (insurance company) and are matched to the unique identifier for each patient's laboratory test results. The patient data is further advantageously organized by the date of service for collected test results and grouped in chronological order by patient. Further, for each blood test result, or each physical measurement, the range for normal values is displayed in adjacent columns to each blood test result. In adjacent columns to each blood test result, a Z-score for each patient's test value is computed based on the normal range of values for a healthy population within each laboratory where the test result was performed and displayed. The Z-score is determined as:

$$Z\text{-score} = (\text{patient test value} - \text{mean normal range value})/\text{standard deviation for the normal range} \quad (\text{Eq. 4})$$

Different laboratories may have different normal ranges. However, all ranges are based on the premise that approximately 96% of a normal population falls within these ranges. Therefore subtracting the low range value from the high range value and dividing by four reveals the standard deviation. The middle range value represents the normal population mean value. In order to display a wide spectrum of Z-score values on the same graph scale, the absolute values for Z scores are converted into logarithm base two values. Converting Z-scores to logarithms facilitates the display of a wide range of very divergent values on the same uniquely constructed radar graph.

For each patient, on each date of service, the following sub-steps are performed. Z-scores greater than the mean are represented as positive numbers. Z-scores below the mean are represented as negative numbers. Disease states result in test values which may produce values that are above or below the normal mean values. Fortunately for each disease, the values measuring increasing severity are generally in one direction (either greater than or less than). For example, in diabetes, blood glucose values increase in a positive direction away from the mean. However in anemia, blood hemoglobin values fall below the mean in a negative direction. Since logarithm values cannot be taken on negative numbers it is necessary to take the log value of the absolute value for negative Z-scores (multiple negative values by −1).

Following determination of the Z-scores, a linear regression calculation is performed on a population of patients with the confirmed diagnosis for the selected disease or syndrome of diseases along with the total weekly/monthly or yearly paid claims for all healthcare expenses spent on caring for each patient. This linear regression calculation will generate a series of Beta coefficients and a significance value (p-value) for each separate test. Next a backward selection process is performed in order to identify the most parsimonious series of tests that are most predictive for required reimbursement dollars. The most parsimonious series of tests are those coefficient values which have a p-value less than a predetermined acceptable value, generally 0.1, to reduce co-linearity (two or more variables having the same effect upon a correlated outcome). For example, if 23 different tests are part of a routine physical examination, and are associated with monitoring the health of a kidney patient with co-morbidities of diabetes, CHF, hypertension, liver disease, and infection, then which of those tests are most significant in predicting the cost of care in that patient? And of those most significant tests, what weighting factors should be given to each test? Is it worse and therefore more costly to have an abnormal liver value or an abnormal kidney value? The Beta coefficient for each variable represents that weighting factor.

Knowing the Beta coefficient (B) for each variable (each test) permits calculation of an ICS based on individual patient test values in the following manner:

The summed value represents the level of illness severity determined by all weighted test values which were abnormal. An ICS of 0 would mean that all tests results for a patient suspected of having disease 1 to 3 were normal, since all tests results had a value identical to the mean reference range. Higher scores represent increasing severity of illness.

$$ICS = D_1(T_{X1...n})*(B_{X1...n}) + D_2(T_{Y1...n})*(B_{Y1...n}) + D_3(T_{Z1...n}) \quad \text{(Eq. 5)}$$

$$ICS = D_1(T_{x_1}) \times B_{x_1} + D_2(T_{x_2}) \times B_{x_2} + D_3(T_{x_3}) \times B_{x_3} = \sum_{n=1}^{3} D_n(T_{x_n}) \times B_{x_n} \quad \text{(Eq. 6)}$$

The ICS is calculated for each patient as the sum of the series for each disease (D) obtained by multiplying the Z-score for each test result by the Beta coefficient for that test. Although the above equations 5 and 6 are characterized by 3 values (i.e., n=1→3), the present concepts include, without limitation:

$$ICS = D_1(T_{X1...n})*(B_{X1...n}) + D_2(T_{Y1...n})*(B_{Y1...n}) + D_3(T_{Z1...n})*(B_{Z1...n}) + ... + D_m(T_{Z1...n})*(B_{Z1...n})$$

$$ICS = \sum_{n=1}^{x} \sum_{m=1}^{y} D_m(T_{x_n}) \times B_{x_n} \quad \text{(Eq. 8)}$$

where m may be equal to or different than n, and x and y may represent any integer.

Plotting the ICS against the natural logarithm for monthly/yearly dollars expended to care for each patient permits comparison of similarly ill patients against dollars expended. In this manner, objective data supports the association between levels of health and dollars to achieve a medical treatment outcome over time.

Thus, a computer system in accord with at least some aspects of the present concepts is configured to utilize one or more processors in one or more locations to perform acts described herein such as, but not limited to, converting each patient's tests to Z-scores, performing a linear regression calculation to generate a series of Beta coefficients and a significance value (p-value) for each separate test, and performing a backward selection process to identify the most parsimonious series of tests that are most predictive for required reimbursement dollars. Further, a computer system in accord with at least some aspects of the present concepts is configured to utilize one or more processors in one or more locations to perform acts described herein such as, but not limited to, calculating an ICS.

The present concepts permit plotting of each patient's test values on separate radar graphs (see, e.g., FIG. 20) for each date of medical service, the following variation is carried out in order to produce a unique and characteristic type of radar plot. First, two radar graph spokes define a wedge area that is divided into three parts from center value (0.0) outwards as follows: (i) log values from 0.1 to 1 are plotted from the center mean value of 0.0 and such values could be highlighted in a first manner, such as being color-coded green. Negative log values are all plotted as value 0.0 since these represent values within the normal range but are in the opposite direction away from the mean; (ii) test Z-scores having log values 1.1 to 2.5 are plotted within their respective wedge and highlighted in a second manner, such as being color-coded yellow; (iii) test Z-scores with log values greater than 2.5 are plotted and highlighted in a third manner, such as being color-coded red. Of course, different color-coding or means of highlighting different severity levels could alternatively be employed to visually differentiate the data presented in the radar plot and the present concepts are not limited to any particular manner of visual differentiation. Second, each wedge in the radar plot represents an individual test result and adjacent wedges are grouped according to tests results diagnostic for pertinent organ systems or conditions. Third, the 12 O'clock wedge advantageously identifies the stage of illness and is defined by medical standards reported in the literature as characteristic for each primary disease. Generally for most disease these stages range zero (for no disease present) to five (for severe end stage disease). These values are not a log value.

Figure 20:
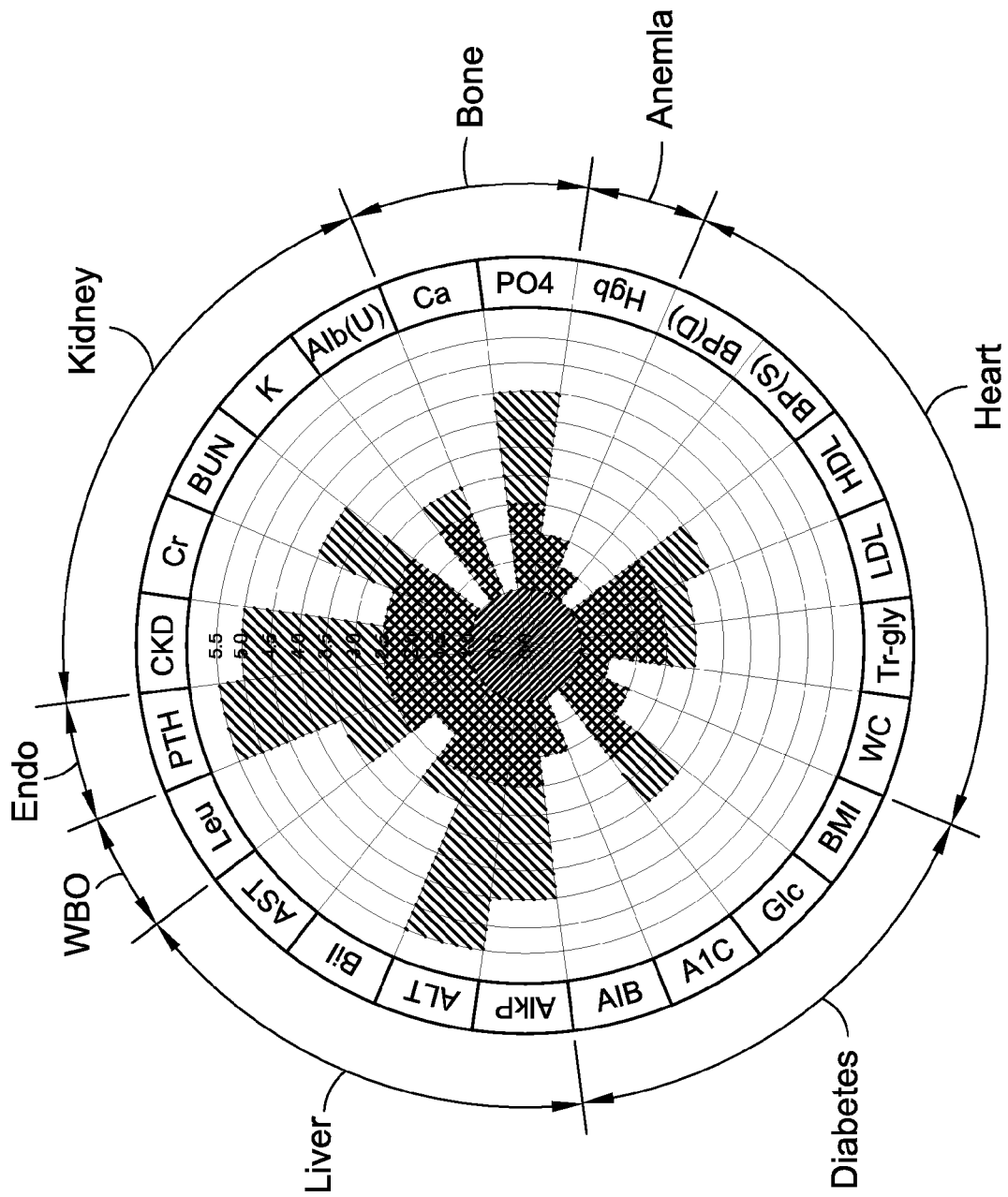
FIG. 20 shows an example of a radar graph for a Stage 5 CKD patient in accord with at least some aspects of the present concepts.

An exemplary radar graph for chronic kidney disease (CKD) in accord with at least some aspects of the present concepts is shown in FIG. 20, which displays the tests which are considered primary for CKD and include, in a clockwise direction starting from the 12 O'clock position: CKD stage, creatinine, BUN, K (potassium), Albumin (Urinary), Ca (calcium), PO4 (Phosphorus), HGB (hemoglobin), BP (Diastolic), BP (systolic), HDL, LDL, triglycerides, waist circumference, BMI, Glu (glucose), A1c, Alb (albumin), AlkP (alkaline phosphate), ALT (alanine aminotransferase), Bil (bilirubin), AST (Aspartate Aminotransferase), Leu (Leukocytes white blood cell count), PTH (parathyroid hormone). In the example of FIG. 20, the radar graph is that of a Stage 5 CKD patient. As presented, each labeled wedge for each test is presented as a meter of deviation from a normal range. In one aspect, the wedges are color-coded to display deviation away from a healthy normal (green) to an increasing degree of illness severity (yellow to red) with increasing distance from the center or normal region of the radar graph. Labels, optionally color-coded, are presented outside the radar wheel or are otherwise disposed about a circumference of the data display of the radar wheel to identify the organ or condition for which the corresponding test name labels pertain.

In some aspects, as patients don't have all tests repeated every time they visit their physician, prior test values are optionally carried forward in the database until replaced by an updated test result. In accord with standards of routine medical practice and medical literature, labels for particular patient's test values carried forward beyond a reasonable period will be flagged in the database and displayed with a contrasting identifier such as, but not limited to, a colored line or strike-through. This alerts the user of the data, such as the patient or provider, as to the potentially out-of-date data and prompt a timely updating of the test.

Although each radar graph can be rendered on-the-fly and generated from stored patient data each time it is requested, each unique radar graph (see, e.g., FIG. 20) is advantageously stored in a database borne on a physical computer readable media so that, via manipulation of an appropriate user-input (e.g., mouse, navigation keys, soft keys, touch screen slider bar, etc.), a user can move forward or backward in time to display and observe changes in the patient's radar graph over time. Radar graphs may be displayed in various ways in accord with user preferences and include, but are not limited to, viewing as a single radar with animation over a chosen period of time or as a film strip of adjacent radar graphs over time. The display device may comprise any computer display or display device, such as a portable mobile reading device or cellular telephone display.

It at least some aspects of the present concepts, the radar graphs are user-customizable so that users can selectively include only certain Z-scores and/or factors indicative of different patient health parameters (e.g., PTH, CKD, CR, BUN, K, CA, PO4, etc.). Thus, a physician that does not need to include ALB, GLC, A1C could selectively remove such sectors from display in the radar graph, such as by eliminating display of the sectors or by, for example, weighting such results so that they are not displayed.

Figure 21A:
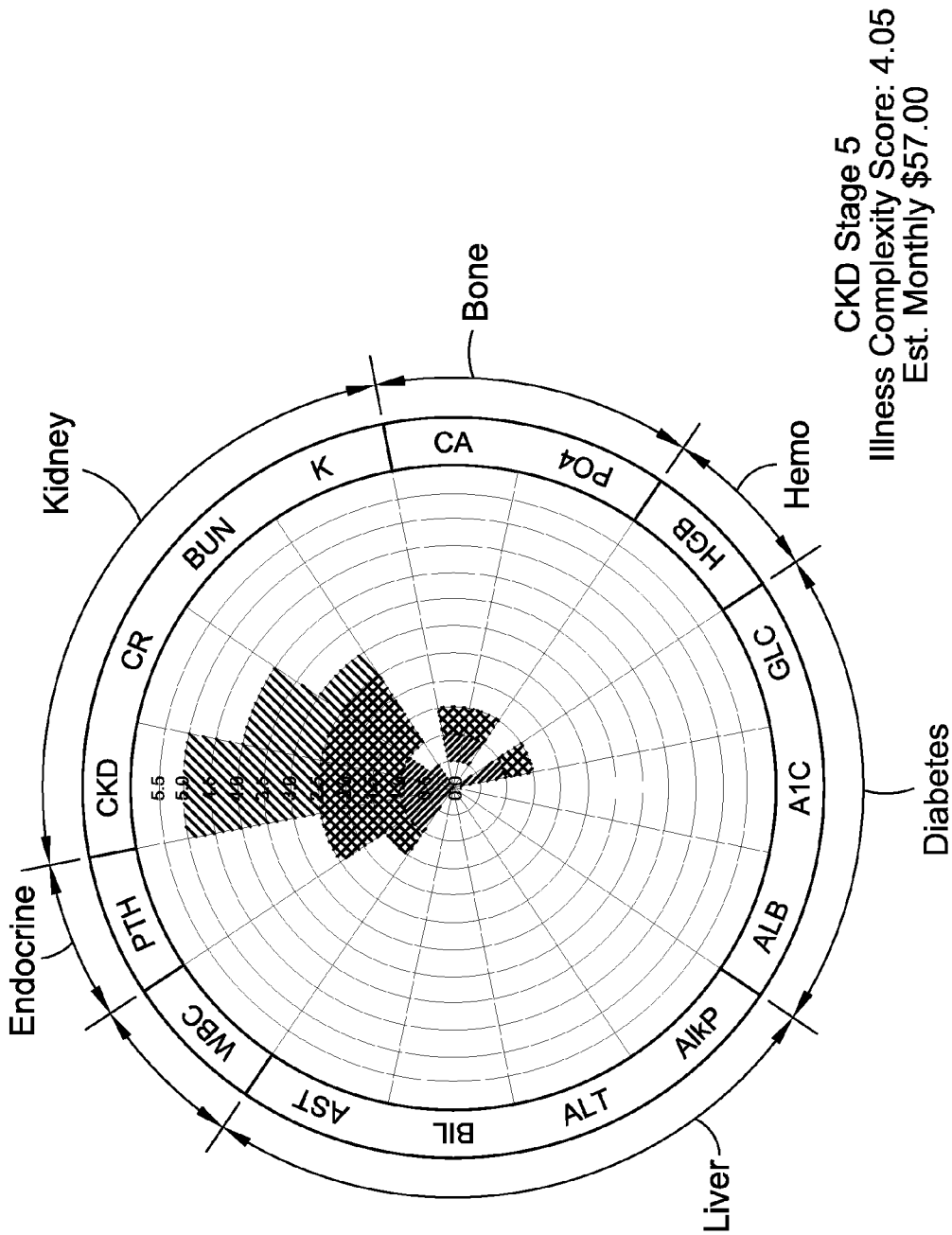
FIGS. 21a-21b respectively show additional examples of radar graphs for a Stage 5 CKD patient in accord with at least some aspects of the present concepts.
Figure 21B:
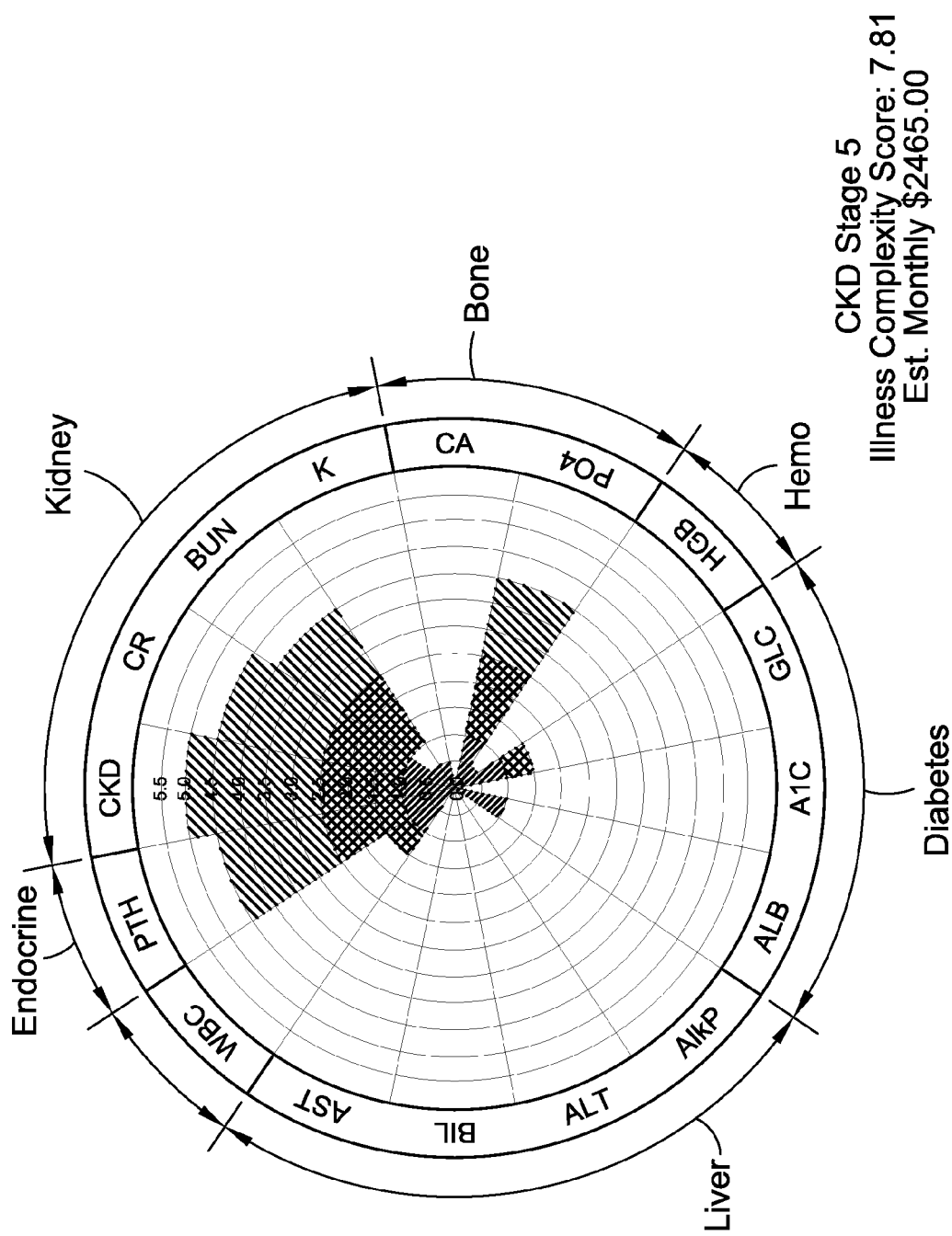

Further, it is to be noted that the radar graphs illustrated in FIGS. 20 and 21A-21B are presented as a full-circle, the present concepts include radar graphs that are arcs circumscribing angles less than 360 degrees, such as but not limited to arcs that are less than 270 degrees, 180 degrees, 90 degrees, or 45 degrees, to reflect varying needs for presentation of information. In this manner, and further in combination with optional user-customization of the radar graph presentation, only information that is immediately relevant to the user need be presented.

With select blood test results and physical measures, which may be obtained during a medical physical examination or which may optionally be obtained an input by a patient, the illness complexity score (ICS) may be calculated. The calculation for ICS employs a linear regression of physician-chosen blood tests and other physical measurements that are considered diagnostic for treatment of patients with a chronic illness and its associated co-morbid conditions. After all patient tests are collected, a series of linear regression calculations are made in order to unmask through a step-wise parsimonious model calculation the key variables related to cost. These calculated key coefficients are then employed as weighting factors to each patient's respective blood test results. In this manner, physical or blood test results having a greater relationship to predicting healthcare cost are identified and given commensurate weight in calculation of a final score.

Next, with the exception of age and eGFR, each blood test result was converted to a Z-score as follows: the mid-point of the normal range for each test was taken as the mean, and the range divided by four as the standard deviation for a non-diseased normal population. Each lab test was standardized using this mean and standard deviation to obtain a Z-score for each variable for each patient. Next the Z-scores for each patient's test results, along with their age, eGFR and all reimbursements in each respective column were averaged by month.

A summary spreadsheet contained 177 lines for each patient's average age, eGFR, average monthly reimbursement, and average Z-scores for all tests over the entire study period. These averaged values for all variables were utilized in a linear regression equation to develop a predictor for average monthly reimbursement in each patient. Graphs and significance levels were calculated on these results. The same regression coefficients used in the preceding equation were also employed to calculate ICS for each patient on each date of service in order to analyze change.

The change in ICS from start to end of the study period was used to cohort the population into three outcome groups: better, same, or worse. Changes in CKD stage from beginning to end of the study period was calculated directly from the laboratory values at date of service.

To test for the relationship between average blood chemistry values, stages of CKD, age, and average monthly reimbursement, we modeled that association through a linear regression function of age, eGFR, and the Z-scores calculated from average monthly values of phosphorus, PTH, glucose, hemoglobin, bicarbonate, albumin, creatinine, urea nitrogen, potassium, calcium, sodium, alkaline phosphatase, ALT, and WBC. A backward selection strategy was then employed to derive a parsimonious model containing only significant predictors. At each step, the explanatory variable with the highest p-value greater than 0.10 was deleted. If its deletion resulted in another variable that had been significant ($p<0.10$) previously becoming non-significant, then the deleted variable was added back into the model and the variable with the next largest p-value greater than 0.10 was deleted. These steps were repeated until only significant variables ($p<0.10$) remained in the model.

These analyses produced a regression table for the final model with an estimated intercept and regression coefficients for each explanatory variable, along with calculated P-values. Next employing the regression coefficients calculated for the most parsimonious variables, these coefficients were employed in a regression equation to calculate a linear predictor by multiplying each appropriate regression coefficient with their respective averaged explanatory variable and summed. The results for each patient were plotted on a scatter plot of ICS versus the natural logarithm for each patient's average monthly reimbursement.

Next, employing the regression coefficients calculated for the most parsimonious variables, an ICS was calculated for each patient on each date of service with no missing variables. As described previously, the regression coefficients used to calculate each ICS on each date of service for each patient were derived from the linear regression calculation for the entire population based on average Z-scores for each patient. The chronological change in illness complexity scores calculated in this way throughout the study period permitted analysis of the relationship of outcome result (i.e., change in ICS) to reimbursement.

Next, the coefficients of the linear regression of the average natural logarithm for monthly reimbursements on average CKD stage categories for each patient over the entire study period were estimated. In a manner similar to developing a linear predictor for multiple blood tests above, the regression coefficient for CKD stage was multiplied with each observed indicator variable for stage and summed with the estimated intercept to produce a predicted value of reimbursement based on stage. Subsequently, these values were plotted in a scatter gram against the average natural logarithm for monthly reimbursement.

Finally, the study pool was sorted by change in ICS from first to last observation month and then divided into three groups: patients with a worse ending ICS, patients with the same start to end ICS, and patients with a better ending ICS. Next the study pool was sorted by change in CKD stage from start to end and divided into the same three groups based on improvement or worsening of stage. The average values for each patient's starting and ending ICS or CKD stage were evaluated by a paired T-Test, and the significance for the change in average reimbursement within each subset was evaluated by an ANOVA calculation. In order to illustrate the predictive power of complexity score as a predictor of average monthly reimbursement, average ICS and CKD stages from start to end of the study period for each patient were plotted in line graphs and compared to a similar plot for the log of average payments. In addition, R-square values were calculated from the linear regressions.

FIG. 4 displays the coefficients and p-values from the regression of the average logarithm of monthly reimbursement on the full set of variables in the table. This regression was based on the sample of 177 patients with observations on all variables analyzed. The overall R-square value from the regression was 0.424 (p=0.000). FIG. 4 shows full test variables before performing of a step-wise parsimonious regression calculation. The variable coefficient for each test or physical measure shown in FIG. 4 is calculated by linear regression. These values are employed as weighting factors to calculate a final ICS. Their values are an indication of how much influence any given test has on the correlation of test value to cost of healthcare. The p-values shown in the rightmost column of FIG. 4 are a measure of the significance each test value has on the correlation of test to cost. Higher weighting values with lower p-values reflect greater influence of the test results on impacting cost. Although the overall p-value for the association of these variables to average monthly cost was significant, nonetheless, as shown in FIG. 4, a number of variables had p-values that were not significant. After a step-wise elimination of the least significant variable at each step, a parsimonious model was obtained and is presented in FIG. 5.

FIG. 5 shows the table of FIG. 4 after performing a step-wise parsimonious regression calculation. The table of FIG. 5 displays the values demonstrating the greatest correlation with cost. Of particular note are the highly significant p-values all below 0.09. This parsimonious set of variables had an overall p-value of 0.00, with an R-square of 41.0% and an adjusted R-square of 37.8%. The association between the ICS derived from this model and the average logarithm for monthly reimbursement for all healthcare services for each patient is shown in the scatter plot of FIG. 1. The average ICSs over the entire study period are displayed on the x-axis, and are derived from the intercept plus a linear predictor derived by the sum of Z-score for each test multiplied by its respective variable coefficient shown in FIG. 5. That is, the ICS was defined as the predicted value of the average logarithm of reimbursement. The average logarithms for monthly reimbursements for all healthcare services are displayed on the y-axis.

In a first step in a process for determining an illness complexity score in accord with aspects of the present concepts, all patients categorized with a primary illness (e.g. CKD, asthma, chronic lung disease, heart disease, etc.) for each database pool are selected. The designation of the primary illness is determined by the primary physician as a part of his/her billing procedure, and is contained within the submitted claims data. In addition, the designation of the primary illness is traditionally employed by insurance companies or payers to group patients within a "disease registry."

In a second step, a relational construct is formed such that selected test values and physical measurements, along with identifying demographics for each patient and their ICD-9 codes and CPT designated procedures, are related. In one example of such a relational construct, a spreadsheet is formed with columns identifying selected test values and physical measurements, along with identifying demographics for each patient and their ICD-9 codes and CPT designated procedures, with rows of the spreadsheet containing test value results sorted and ordered chronologically according to date of service.

In a third step, a series of linear regressions are performed on the entire pool, such as is referred to in relation to FIGS. 4-5, in order to calculate coefficients for the key variables associated with the primary illness and its commonly associated co-morbid conditions.

In a fourth step, the calculated coefficients for each blood test or physical measurement are utilized to compute an illness complexity score (ICS) for each patient on each date of medical service. The ICS is calculated by, first, multiplying each patient's test result for each test by its corresponding calculated variable coefficient (the weighting factor) to weight each test result. Next, these weighted values are summed along with the previously calculated linear regression constant. The sum of this computation is designated as the illness complexity score (ICS) for each patient on each date of service.

In one aspect, the generalized ICS of Equations 7-8 can be determined, in one specific case, as follows:

$$ICS = \text{Sum (constant)} + (Age*VC) + (CKD\ stage*VC) + (Z\text{-score of } PO4*VC) + (Z\text{-score of } HGB*VC) + (Z\text{-score of albumin}*VC) + (Z\text{-score of creatinine}*VC) + (Z\text{-score of } ALT*VC) + (Z\text{-score of } WBC*VC) + (eGFR*VC) \quad \text{(Eq. 9)}$$

where VC (Variable Coef.) is the linear regression of age, CKD Stage, eGFR and the Z-scores calculated from average monthly values for PO4, HGB, albumin, creatinine, ALT and WBC. Thus, for each patient encounter, a single health score can be produced and such health scores can be produced and tracked over time in a manner that is positively related to cost.

In accord with at least some aspects of the present concepts, the ICS is used to plot a line graph to correlate of changes over time in the ICS to cost for each patient. Time values (days, weeks, months) are plotted on the x-axis, while ICS values for each corresponding date are plotted on the y-axis. On the same graph, the total cost for all delivered healthcare services on each date of service is plotted as a natural logarithm value also on the same Y-axis. In this manner, a measure of discrepancy between ICS and cost is visualized. If cost and ICS are closely matched, both variables will move synchronously and close together in values. If cost is higher than ICS, this may indicate overpayment, while conversely if cost is well below ICS, it may suggest underpayment.

Figure 6:
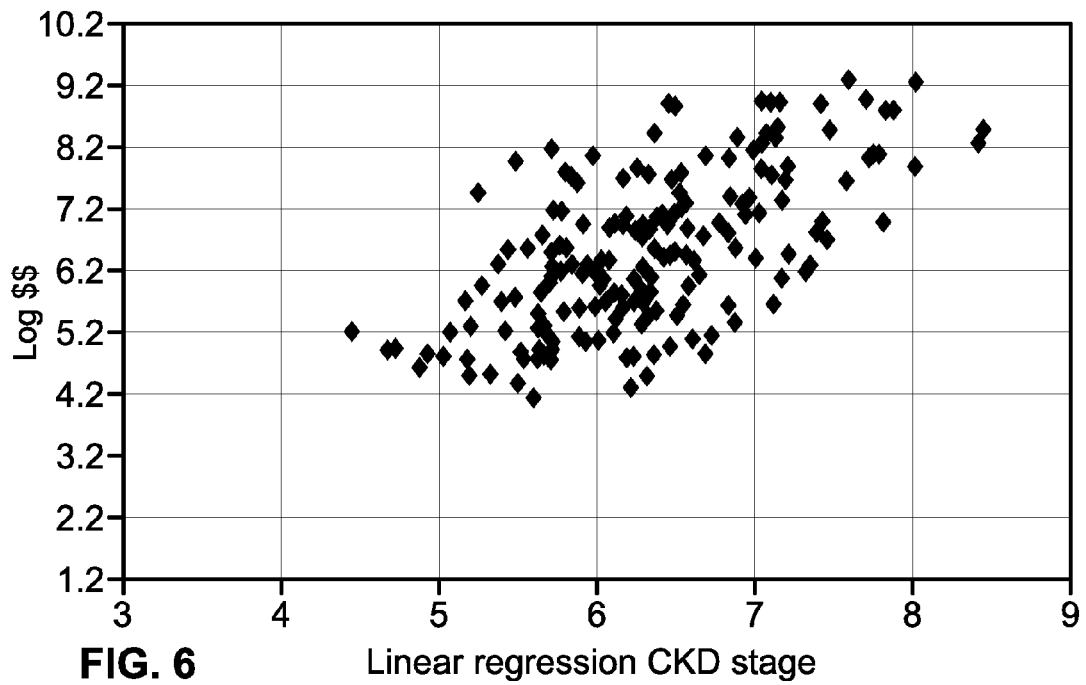
FIG. 6 is a scatter plot of illness complexity score (higher ICS with increasing distance from origin along x-axis) against log values for dollars of average monthly reimbursement (higher values with increasing distance from origin along y-axis) in accord with at least some aspects of the present concepts.

In accord with at least some aspects of the present concepts, the average monthly illness complexity scores (ICSs) for patients classified within the same disease registry are plotted (X-axis) against the natural logarithm of average monthly total cost (Y-axis) for all delivered healthcare services, such as is shown by way of example in FIG. 6. In FIG. 6, each of the 177 diamonds represents a year of treatment for a single CKD patient, increasing values along the X-axis represent greater levels of illness complexity (Linear Predictor ICS), and increasing values along the Y-axis display the log average monthly values for dollars (e.g., log 4=$55 monthly; log 8=$2,981 monthly; log 9.0=$8,000 monthly). In FIG. 6, complexity scores ranged from 4.45 to 8.45 (x-axis) and were associated with increasing average monthly reimbursements: 4.11 to 9.26, ($61 to $10,509) (y-axis).

FIG. 6 illustrates not only that rising illness complexity scores are associated with increasing average monthly expenditures for healthcare services, but also reveals, as shown by the upward trend line, a correlation between increasing ICS and higher corresponding cost with an $R^2=0.41$. The R-square value for the relationship between illness complexity scores and the average natural logarithm for monthly reimbursement for all healthcare services is 41.0%.

Although there is a wide variation in cost associated with any single illness complexity score, the range for reimbursements based on ICSs ranged from 4.11 to 9.26 and represented dollar amounts of $61 to $10,509. Evaluating the range of reimbursements for patients sorted by CKD stage as shown in the linear regression weighted values in FIG. 7, their range was identical to that seen in FIG. 1: 4.11 ($61) to 9.26 ($10,509). However, the extremes of this range was observed in two patients both classified as CKD stage 3-B. Illuminating this weak association of CKD stage to reimbursement is an R-square calculation equal to 0.083. The result in FIG. 6 is to be contrasted to the scatter plot shown in FIG. 7 for the same CKD population, but sorted by average CKD stage for each patient over the study period. Average values for CKD stages based on a calculated eGFR (MDR4) and weighted by their regression coefficient are displayed on the x-axis, while the average natural logarithm for monthly reimbursement for all healthcare services is shown on the y-axis.

Figure 7:
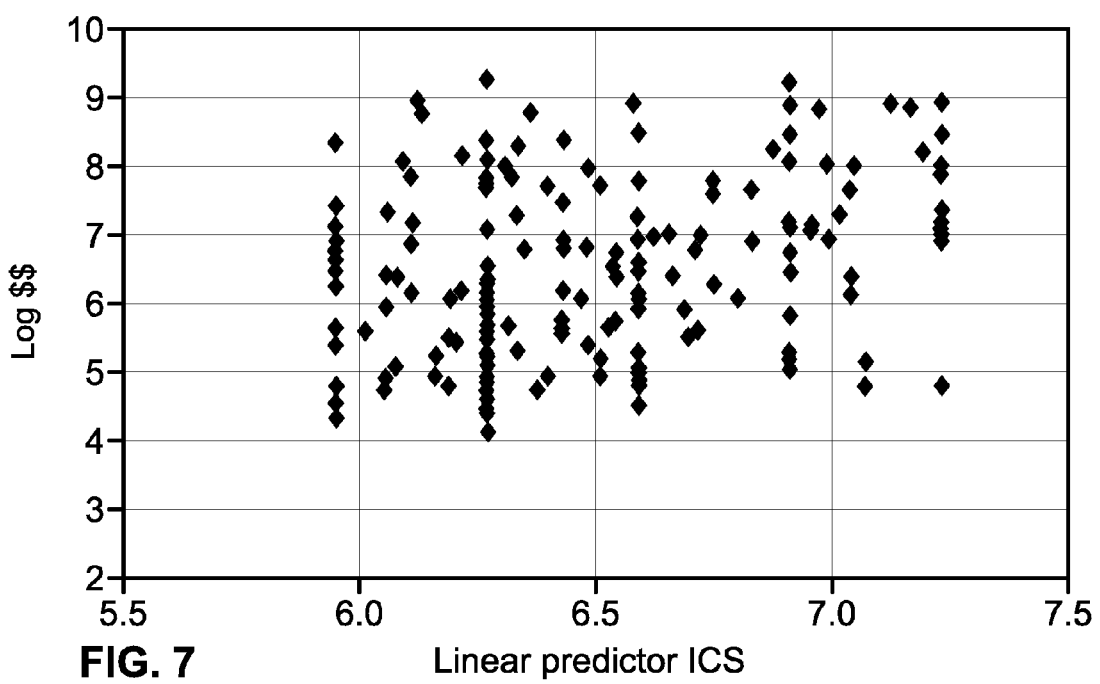
FIG. 7 is a scatter plot showing the linear progression values calculated for stage of illness only in accord with at least some aspects of the present concepts.
Figure 15:
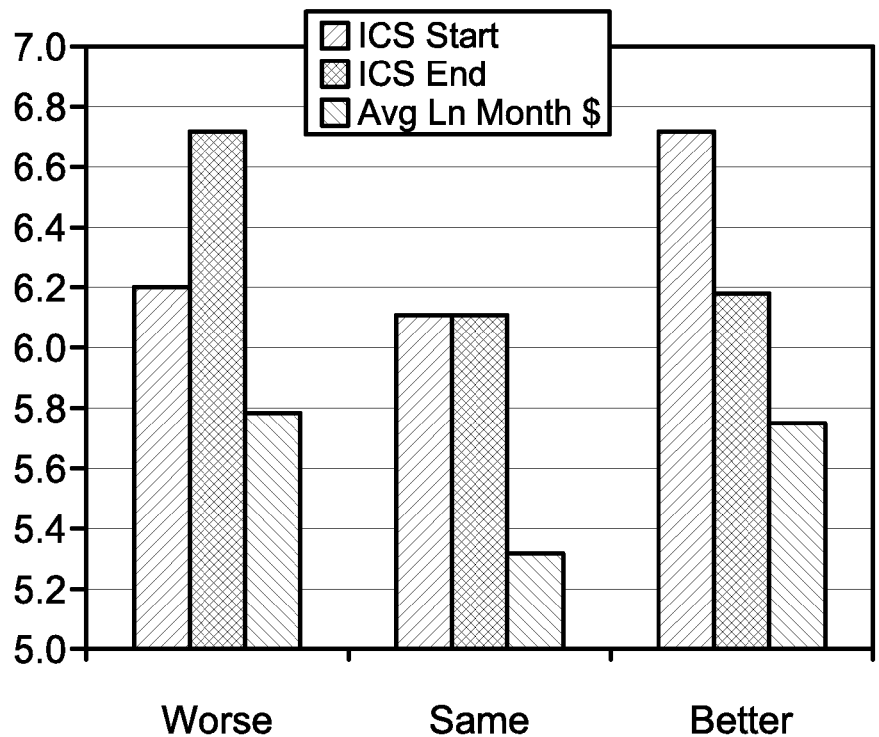
FIG. 15 is an exemplary histogram for change in illness complexity scores and reimbursement over a study period in accord with at least some aspects of the present concepts.
Figure 16:
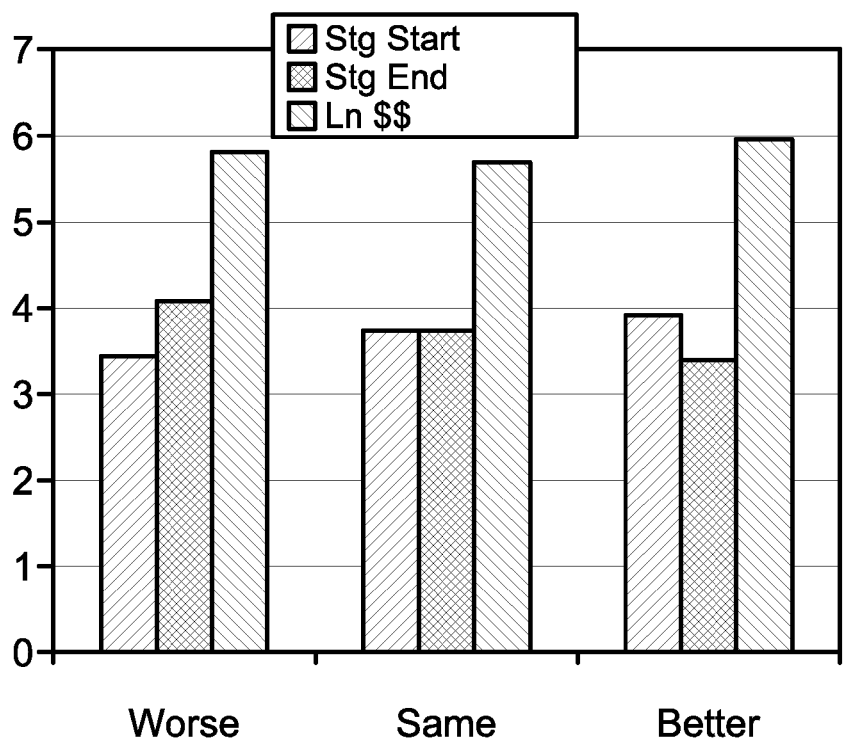
FIG. 16 is an exemplary histogram for change in CKD stage and reimbursement over a study period in accord with at least some aspects of the present concepts.

The variation in average monthly dollars for all four CKD stages shown in FIG. 7 varies from 4.11 to 9.26 ($61 to $10,509). Interestingly, this widest range of reimbursements was seen in the vertically aggregated diamonds seen at x-axis=6.27 which is associated with CKD Stage 3-B. The linear regression for the association between average stage of CKD and average monthly reimbursement demonstrated an R-square value of 8.3% with an adjusted R-square of 7.8%. In order to evaluate changes observed in ICS and CKD stage over the entire study period and to correlate those changes to reimbursement, the patient pool was sorted by change in both ICS and CKD stage from first to last observation and compared to their respective average monthly reimbursements. These results are shown in FIGS. 15 and 16.

Figure 8:
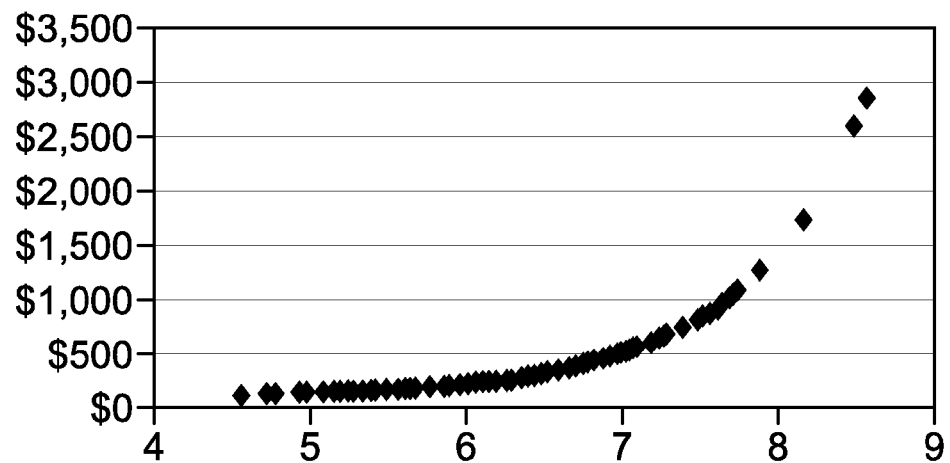
FIG. 8 is a plot of the predicted average monthly cost (y-axis) versus each patient's linear predictor in accord with at least some aspects of the present concepts.

FIG. 8 likewise shows a plot of illness risk versus cost, with predicted average monthly cost (y-axis) plotted versus each patient's linear predictor (x-axis).

The plot in FIG. 6 may be contrasted to the scatter plot in FIG. 7 for the same patients, which shows the linear progression values calculated for stage of illness only. Since payers and patients traditionally view their health outcomes by progression of stage and assume a relationship of increasing stage to higher cost, that display is shown in FIG. 7. The scatter plot of FIG. 7 illustrates a poor correlation of increasing stage of disease (X-axis) to increasing log dollars (Y-axis). The distribution above highlights the problem confronting payers in determining fair compensation for providers who care for patients classified within a single ordinal stage of illness. Another way to view this same conclusion is shown in the box and whisker plot of CKD patients presented in FIG. 3. As previously noted, the box and whisker plot displays on the X-axis the various stages of CKD (1-5), with the Y-axis displaying the natural logarithm of the weighted values for ICS and, across any horizontal line from the Y-axis, patients in a lower stage of CKD can have illness complexity scores associated with higher stages of CKD.

Figure 19:
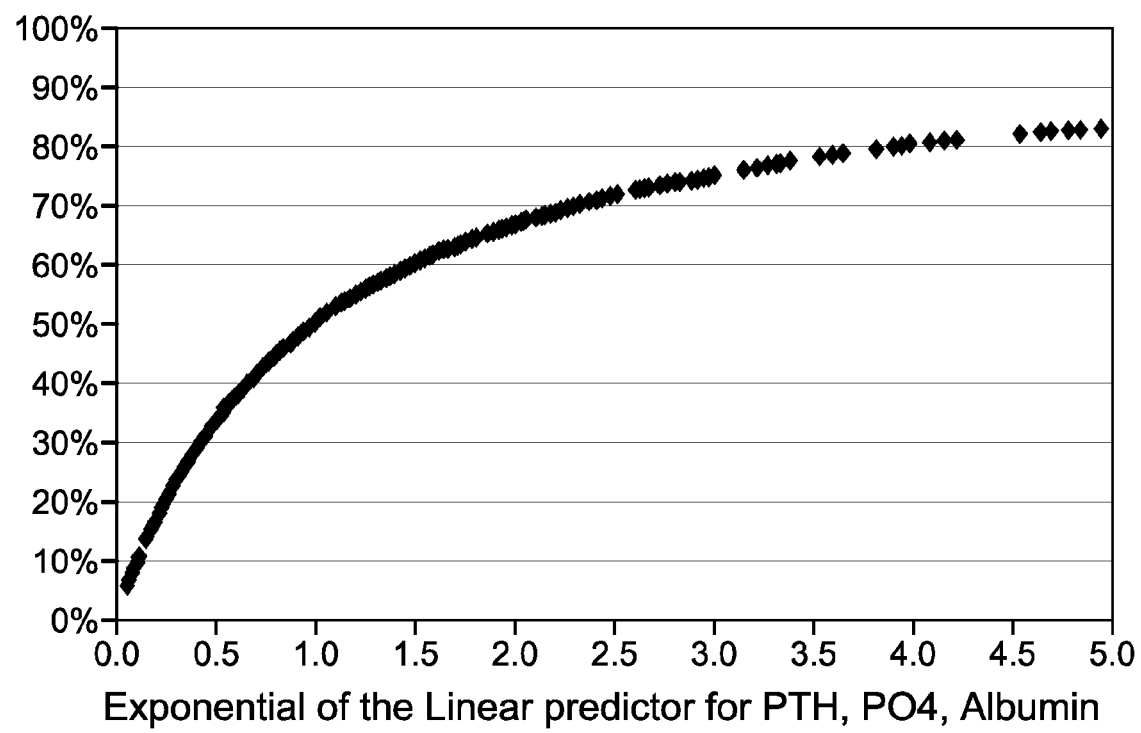
FIG. 19 is a graph showing risk for high-cost care (y-axis) in relation to an exponential of the linear predictor for PTH, PO4 and Albumin (x-axis) in accord with at least some aspects of the present concepts.

Since both patients and payers have difficulty in visualizing differences in illness complexity between two patients with the same stage of disease, the methods and systems disclosed herein permit distribution of patients along a complexity scale compared to cost. By way of example, FIG. 19 presents a plot illustrating the risk for high-cost care based on a study performed of 267 patients over a treatment period of 13 months. The y-axis represents the percentage probability for high-cost care greater than $3,000 in any single month versus the magnitude of the linear predictor for PTH, PO4 and Albumin.

In addition, the methods and systems disclosed herein are able to readily highlight the differences between individuals with the same disease stage, but different illness complexity, such as is shown in the examples of FIGS. 21A-21B, each of which represents a single patient having stage 5 CKD. As is evident from even casual comparison of FIGS. 21A-21B, the graphical presentations of each patient's data are different. The illness complexity score for the patient of FIG. 21A is seen as 4.05, while the illness complexity score for the patient of FIG. 21B, which presents elevated PO4, BUN, CR and PTH, is seen as 7.81. The estimated monthly cost for these two patients is, respectively, $57 versus $2,465, a significant different even though the stage of CKD is the same.

Returning to the aforementioned calculation of ROI for each patient's outcome over time (see Eq. 1), the utilization of the ICS therein is described below with reference to three patients. Patient A began a period of chronic illness with an ICS score of 7.6 and three months later had a score of 5.6. The average monthly cost for all medical expenses for this patient was $403 (natural log value 6.0). ROI*100=((7.6−5.6)/3))/6.0, therefore yielding an ROI=11.1%. Patient B began a period of chronic illness with the same ICS score of 7.6 and three months later had a score of 6.2 with an average monthly cost of $148 (Ln 5.0). Her ROI*100=((7.6−6.2)/3))/5.0. Therefore, her ROI=9.3%. Patient C also began a period of illness with an ICS score of 7.6 and three months later had a score of 8.2 with an average monthly cost of $1,097 (Ln 7). His ROI*100=((7.6−8.2)/3))/7.0. Therefore, his ROI=[−2.9%].

Figure 9:
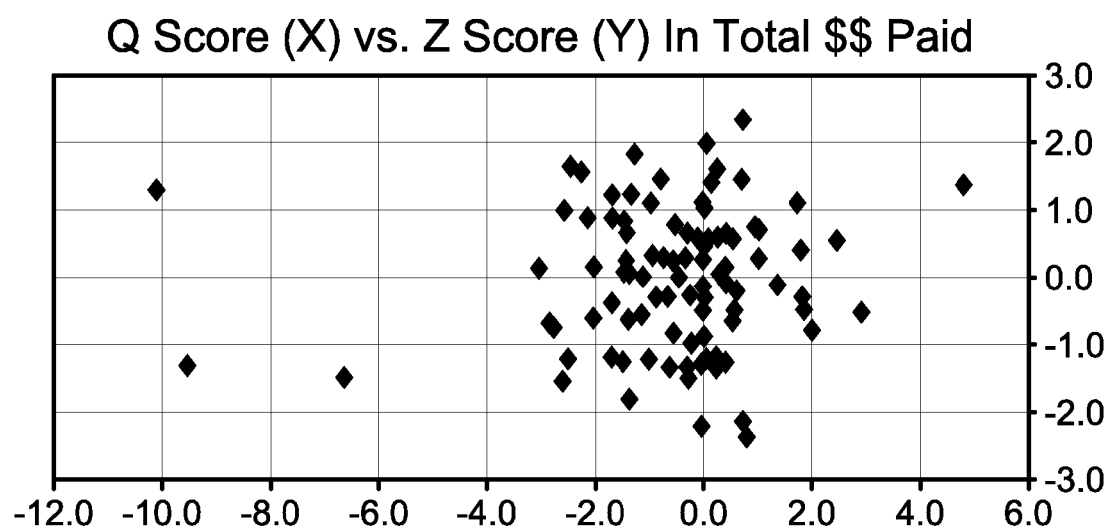
FIG. 9 is a graph of Q score on the x-axis (which is each patient's starting ICS minus their ending ICS) and the Z score (for each patient's average monthly cost compared to the population mean for cost) on the y-axis in accord with at least some aspects of the present concepts.
Figure 10:
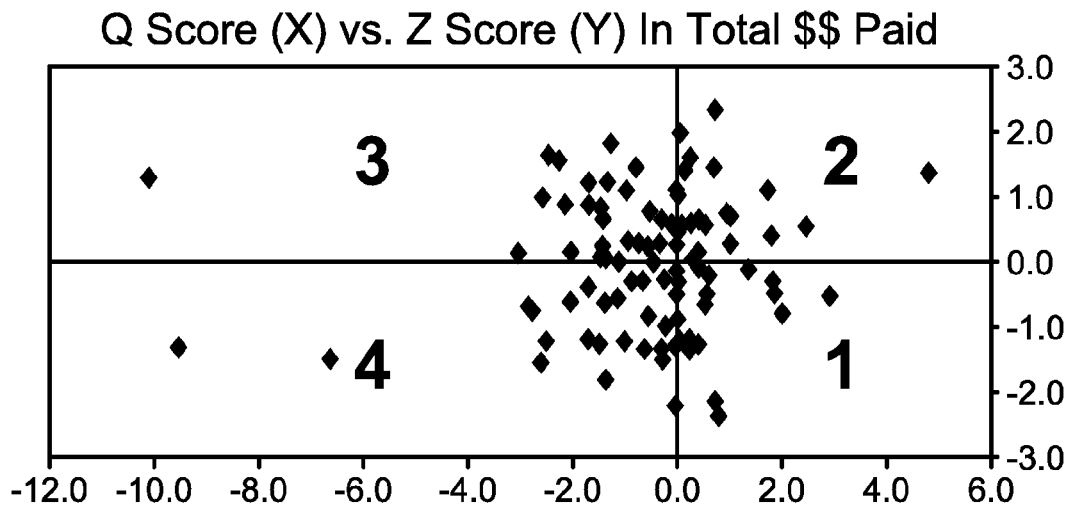
FIG. 10 is the graph in FIG. 9 segmented into four quadrants in accord with at least some aspects of the present concepts.
Figure 11:
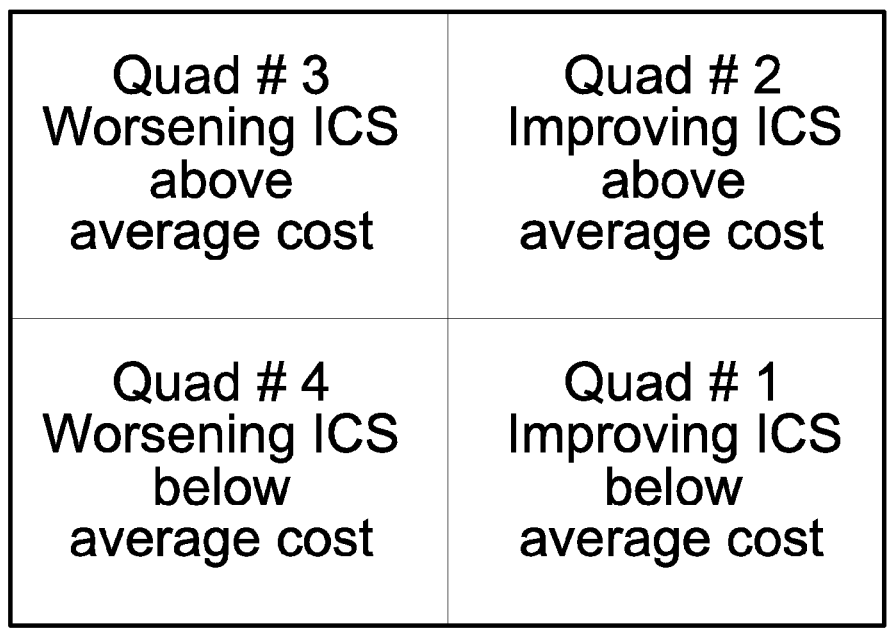
FIG. 11 is an explanation of the four quadrants of the graph showing relationships between ICS and cost of FIG. 10 in accord with at least some aspects of the present concepts.

Further, in accord with at least some aspects of the present concepts, a "Q Score" or "Quality Score" plot may also be generated. Since ROI reports health outcome versus cost achieved in individual patients, the present methods and systems are further utilizable to segregate a population of patients into outcome groups. In order to accomplish this, the present methods and systems perform analyses represented in FIGS. 9-11. In FIGS. 9-11, a patient population is divided into pools based on a common designator such as, but not limited to, stage of illness, primary provider, treatment choice, etcetera. For each pool type (e.g. stage of illness), a scatter plot is generated such that (i) along the x-axis, each patient's change in ICS is plotted (Start ICS−End ICS) and (ii) along the y-axis, the Z-score for each patient's average monthly cost is plotted. The Z-score for average monthly cost is calculated by determining the average monthly cost and standard deviation within a pool of patients grouped by disease stage (1-5).

When these results are plotted on a scatter graph, such as is shown in FIGS. 9-10, values falling on the central crossing point of the graph (0.0) reflect no change from start to ending ICS, and were achieved at the average cost for that pool. FIG. 10 divides the scatter plot of FIG. 9 into quadrants, with plot points in Quadrant 1 (lower right) displaying patients with varying degrees of health improvement in ICS achieved at below average cost, plot points in Quadrant 2 (upper right) displaying patients with varying degrees of health improvement achieved at above average cost, plot points in Quadrant 3 (upper left) displaying patients with varying degrees of worsening health outcome over time at above average cost, and plot points in Quadrant 4 (lower left) displaying patients with varying degrees of worsening health outcome over time at below average cost. This differentiation is summarized in FIG. 11.

Figure 12:
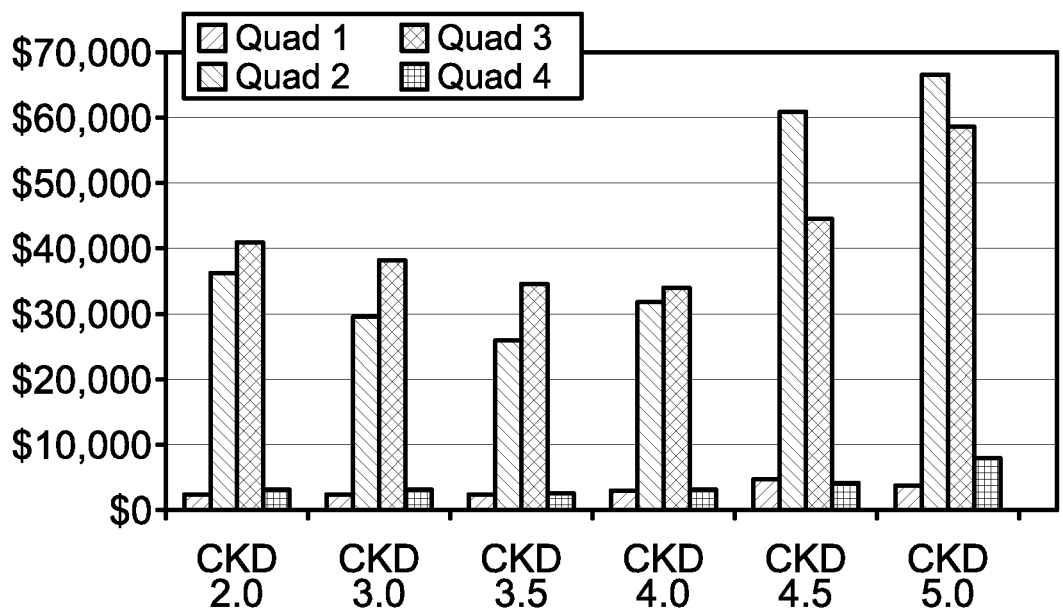
FIG. 12 is a bar graph demonstrating the relative cost and health of patient outcomes in FIG. 10 in accord with at least some aspects of the present concepts.

FIG. 12 is a bar graph demonstrating that Quad 3 are the outcomes that provide the worst healthcare outcomes, i.e., worst patient health matched with high cost, whereas Quad 1 (bar one) provides the ideal, improving health with below average cost.

In one advantageous implementation of the present concepts embodied in the Q Score plot of FIG. 10, a user of the system (e.g., a medical care provider, an insurance company, etc.) may use an input device (e.g., touch screen, mouse, navigation key, voice command, etc.) to operatively select an individual patient data point (e.g., the outlier at the left side of Quad 3) to pull up additional patient data, such as may be represented by the radar graphs depicted by way of example in FIGS. 20 and 21A-21B herein. Alternatively presentations of patient data for the selected patient could additionally or optionally including any other manner of static or time-based (or time-lapsed) plots, graphs, charts, spreadsheets, contact information, hyperlinks, hypertext, figures, etcetera.

The Q score also provides individual provider scores based on the treatment measure by improvement in health/time; and that is plotted against cost to achieve those results among providers who treated similar levels of patient illnesses.

Figure 13:
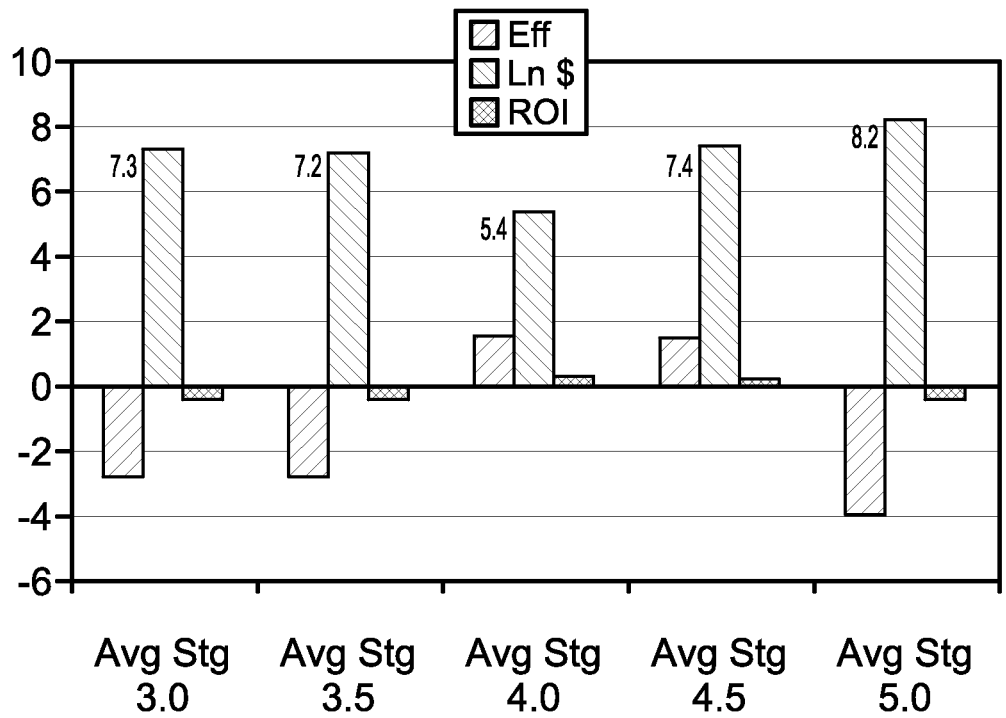
FIG. 13 is a bar graph demonstrating the efficiency and ROI of a particular doctor in accord with at least some aspects of the present concepts.
Figure 14:
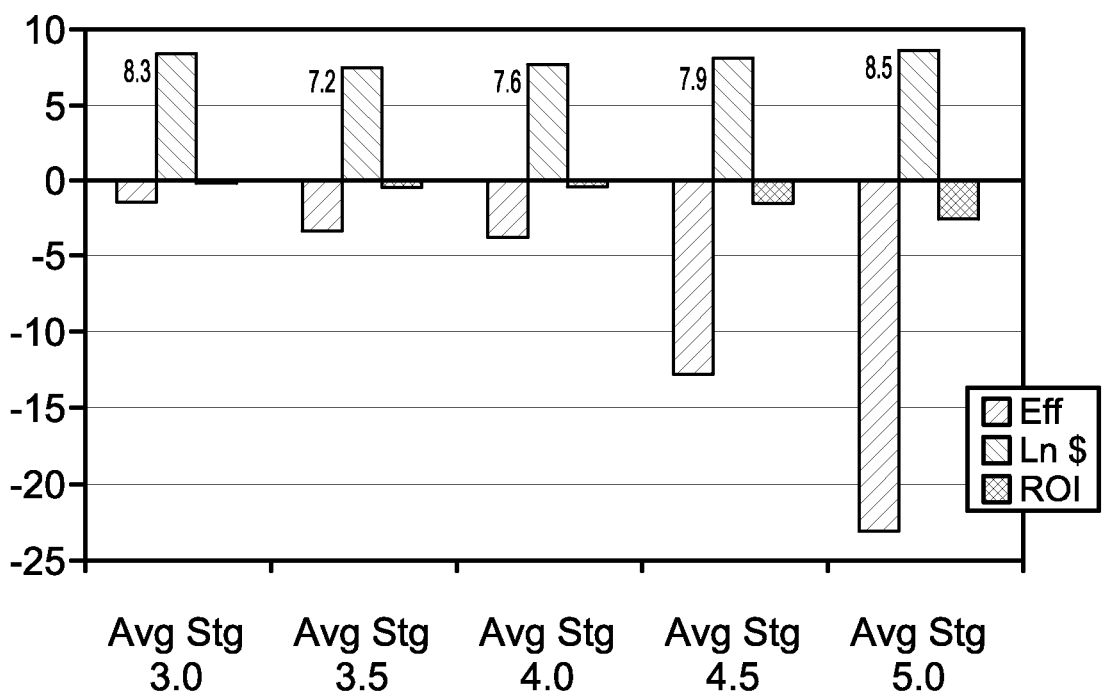
FIG. 14 is another bar graph demonstrating the efficiency and ROI of another particular doctor in accord with at least some aspects of the present concepts.

FIG. 13 is graph that demonstrated the relative efficiency of a first doctor, where efficiency is ICS/time of RX and ROI=efficiency/ln $. FIG. 14 is a second doctor efficiency graph using the same variables. In this manner, insurance payers are able to assess individual provider treatment outcomes for patients grouped by similar illness complexity levels and thus identify preferred provider networks and set risk-adjusted fees.

FIG. 15 is a histogram demonstrating the average reimbursement for all healthcare services for the patient pool sorted by worse, same or better ending ICSs, showing bars representing average complexity scores at the start of the study period, average scores at the end of the study period, and the average natural logarithm for total monthly payments.

The 86 patients with a worse ending ICS had an increase from a start of 6.20 to an ending value of 6.72. The 30 patients with no change in their ICSs from start to end had an average score of 6.11. The 61 patients with illness complexity scores that improved over the study period had values that began at 6.71 and decreased to 6.18. A paired T-Test for comparison of the change from start to end demonstrated that both the worse ending and better ending cohorts had significant differences at p-value=0.00.

The average monthly reimbursements for all healthcare services in each group (worse, same, or better) was 5.79 ($327), 5.32 ($204), and 5.75 ($311) respectively. A one way ANOVA calculation for differences in the average monthly reimbursement for patients with worse ending ICSs compared to patients with same starting and ending scores demonstrated significance at p-value=0.05. The one-way ANOVA test for comparison of differences between average monthly reimbursements in patients with worse ending scores to those with better ending scores had a p-value=0.78.

In contrast, FIG. 16 is a histogram for the same patient population, but sorted by a worse, same, or better ending CKD stage. The x-axis is the same as in the previous figure, and the y-axis displays the average value for changes in CKD stage within each group as well as the average logarithm for total monthly reimbursement.

The 30 patients with a worse ending CKD stage had an average stage change from 3.45 to 4.10. The 122 patients that remained at their same stage had an average value of 3.76. The 25 patients with an improved ending stage had a change from 3.94 to 3.42.

A paired T-Test for the change in average stage in both the worse and better ending cohorts demonstrated significance at p-value=0.00. However the ANOVA calculation for the difference in average monthly reimbursement among any of the three groups revealed no significant differences between worse and same, or same and better ending, p-value=0.50 and p-value=0.26 respectively. The difference between same ending and better ending CKD stage was not significant at p-value=0.68.

The average monthly reimbursement for all three groups of Worse, Same, or Better was 5.84 ($344), 5.71 ($302), and 5.96 ($388) respectively.

In order to compare the relationship between average ICS and average CKD stage to the average natural logarithm for monthly reimbursement in each patient, the two patient pools were rank ordered by reimbursement amount from smallest to largest and plotted by line graphs as shown in FIGS. 5 and 6.

FIG. 17 is the line graph for 177 patients displaying the relationship between ICS and the average natural logarithm for total monthly reimbursements. The irregular red line depicts ICS values (y-axis) for each patient displayed on the x-axis. The slightly sigmoid line illustrates the values for the natural logarithm of average monthly reimbursements for each patient (also on the y-axis scale). The linear trend for these scores was from an ICS value of 5.6 to 7.7. As suggested by the R-square value of 41%, there is correlation of the predicted ICS values to average monthly reimbursement in the mid-range of the line graphs with a symmetrical divergence of ICS values at both the upper and lower regions of the graph.

In contrast, FIG. 18 demonstrates the line graph comparing average CKD stage to the average natural logarithm for monthly reimbursements in 177 patients. The linear trend line for the beta weighted average stages of CKD ranged from a value of 6.2 to 6.9 with an R-square value of 8.3%. The small correlation of weighted CKD stage values with the line plot for average reimbursement demonstrates this predicted relationship with wide divergence of the ICS predicted values from the average monthly reimbursements.

As patients, payers, and elected officials seek to improve the public health and lower healthcare costs, there is the need to understand the correlation between illness complexity, outcome and reimbursement. Recent legislation to reform healthcare and provide universal coverage mandates a shift in provider compensation to a system that rewards value-based outcomes. Generally, when payment for professional services is considered, costs are expected to parallel problem complexity, that is: the more severe the problem, the higher the expected cost. Conversely, if the problem is routine, so is the expected fee. Based on this assumption, a goal was to utilize routine blood test measures and analyze their association with predicted costs. In addition, a derivative of those measures was evaluated to score illness complexity (ICS) with a single numeric value that had a reliable relationship with reimbursement, and might offer more information about disease severity than CKD staging alone. The results of the study demonstrated that the association between average ICS values throughout the entire study period predicted average monthly reimbursements with an R-square value of 41.0%. Comparing that value to the association between the average CKD stage to average monthly reimbursement revealed an R-square value of 8.3%. Thus, the ICS offers five times greater sensitivity over CKD staging as a measure of illness complexity.

A major concern for payers, under any system, is that providers will revert to a fee-for-service concept, which incentivizes the use of more services. Without reliable, objective measuring tools to score illness complexity and outcome, both providers and payers must depend on subjective anecdotal arguments to debate disagreements on reimbursement. Without reliable data to predict likely treatment outcomes, risk-adjusted capitation agreements as part of a future ACO will pose a challenge. As a result, payers will be constrained to continue judging quality and reimbursement based primarily on claims data for any given illness. Alternatively, they may divide the claims data into deciles and pay providers within a range of chosen deciles. Such systems are population based and do not consider individual patient variation or outcome.

A measuring tool that recognizes illness complexity at the start and end of treatment in CKD patients, while still respecting the concerns of over utilization in healthcare services, can augment current metrics that base provider payment upon ordinal staging of CKD. An exemplary illness complexity score (ICS) according to the present invention is derived from the summation of the linear regression for an equation constant, patient age, and select serum chemistry values, which produced a single score based on the deviation of blood tests from their normal mean. The regression coefficients were calculated from a linear regression of average Z-scores for each blood test for each patient in the study pool versus the natural logarithm of average total monthly reimbursements for those same patients. The resultant regression coefficients were then subsequently used to weight the most significant blood test results shown in FIG. 5 for any patient on any single date of service. The final illness complexity score (ICS) for any given date of service was based on these weighted factors. With future access to larger data pools, with more longitudinal observations for each variable, we believe the reliability for these coefficients could be improved.

The staging of renal disease by a calculated eGFR is a gold standard for evaluating patients with kidney dysfunction. However, determining payment for healthcare services based primarily on this measure may not illuminate the impact of co-morbid conditions, or account for different outcomes influenced by additional illness complexity. Though there are many other tests, which one could employ in a CKD population, the present study was restricted to those serum chemistry values considered by the consulting nephrologists to be important in monitoring CKD patients, and importantly were often ordered by primary care physicians as part of a routine blood panel.

With expanded use of electronic health records and availability of physical measurements, such as systolic blood pressure, BMI, micro-albuminuria, and cardiac function studies, which could be added to the linear predictors employed in this study, we believe the relationship between ICSs and reimbursement can be further improved.

The concepts disclosed herein demonstrate the potential for ICS values to illustrate changes in objective blood tests results after treatment. When the patient pool was sorted by improved, same, or worse ending ICSs, there were significant changes observed in both the improved and worse ending ICS values (p-values=0.00 and 0.00). In addition, the difference in reimbursements between the ICS worse ending group compared to the same ending group, or the better ending compared to same ending group demonstrated slightly significant differences at p-values=0.05 and 0.07 respectively. As expected, patients within the worse ending ICS group demonstrated the highest average expenditures.

FIG. 16 demonstrates that when the population is sorted by changes in CKD stage from start to end of the study period, a paired T-Test demonstrated a significant difference in both the worse ending and better ending CKD stage groups (p-values=0.00 and 0.00). However, the difference in average monthly reimbursement for all three outcomes groups did not demonstrate a significant difference from the average reimbursement for the same ending stage group (ANOVA p-values=0.50 and 0.68).

Furthermore, division of the patient pool by changes in CKD staging over the entire study period demonstrated that 122 of 177 patients (68.9% of the total population) had no change in stage. In contrast, 30 patients (16.9%) ended the study period with the same starting ICS. Comparing CKD stage improvement to ICS improvement: 25 patients (14.1%) improved their stage, while 61 patients (34.4%) improved their ICS. There were 30 patients (16.9%) with a worse ending CKD stage, and 86 patients (48.5%) with a worse ending ICS. The changes observed in ICS scoring over the entire study period produce a more sensitive measure to change in health status which is more consistent with clinical experience. That is: CKD is a chronic progressive disease generally associated with diminishing health, which must be carefully monitored. The percent shift in worsening health for this study's population, 48.5% for ICS monitoring versus 16.9% for CKD stage monitoring, supports clinical experience. Use of ICS may allow evaluation of the reasons for changes in the score (e.g., improvements resulting from provider selection or treatment choices).

FIG. 17 demonstrated that when the linear regression for the averaged Z-scores for each patient is employed in a linear equation calculation, the resultant summation for each patient demonstrates a reasonable predictive correlation (R-square=41%) with the natural logarithm of average monthly reimbursements. This was contrasted to results of FIG. 18 for a linear equation summation for average CKD stages in each patient to the natural logarithm of average monthly reimbursements.

The present concepts are implementable on a conventional computer system of any form, whether a work-station, laptop, tablet or handheld electronic device (e.g., smart phone) comprising a bus or other communication mechanism for communicating information, and a processor or processors coupled with the bus for processing information. Such computer system includes a main memory, such as a random access memory (RAM) or other dynamic storage device, coupled to bus for storing information and instructions to be executed by the processor(s). The main memory also may be used for storing temporary variables or other intermediate information during execution of instructions to be executed by the processor(s). The computer system further includes a read only memory (ROM) or other static storage device coupled to bus for storing static information and instructions for the processor(s). External storage devices such as a thumb drive or flash drive may also be coupled to the bus for storing information and/or instructions. The computer system further comprises a display device to display information to a computer user and one or more input devices, including alphanumeric and other keys, a mouse, a trackball, navigation keys, touch screen, voice command, etcetera.

The present concepts relate not only to the methodology described herein, but also to the use of such computer system to implement and perform such methodology. The computer system, in response to processor(s) executing one or more sequences of one or more instructions according to the disclosed concepts, based on instructions read into the main memory from a physical computer-readable medium (e.g., non-volatile media, volatile media, etc.).

Portions of methodology disclosed herein may be optionally implemented across a plurality of different computers or computer systems in one or more than one location. In this way, processing may be distributed with the results being available, in the aggregate, at a single location. The computer system includes a communication interface which provides a two-way data communication coupling to a local and/or remote computer or network (e.g., an integrated services digital network (ISDN) card, modem, local area network (LAN) card, wireless link, etc.). For example, a network link provides data communication through one or more networks to other data devices, such as to a local network host computer or to data equipment operated by an Internet Service Provider (ISP), which ISP would in turn provides data communication services through the Internet. Thus, in accord with at least some aspects of the present concepts, a server might transmit data and/or instructions relating to the presently disclosed concepts through the Internet, one or more ISPs, and a local network to the communication interface.

While this method and system has been shown and described with reference to certain preferred embodiments thereof, it will be understood by those skilled in the art that various changes in form and details may be made therein without departing from the spirit and scope of the invention as described. For example, the present concepts, although described in relation to human patients, is equally applicable to animals, such as cattle (cows, sheep, etc.), horses, dairy cows, or even family pets (e.g., dogs, cats, etc.). Yet further, the present concepts, such as but not limited to the radar graph of FIG. 20, can be adapted to health measures for other physical conditions, such as pregnancy, and can be still further adapted to separately assess health measures for both mother and baby in utero (e.g., sonogram measurements, etc.).

What is claimed is:

1. A method for presenting patient test data on a display device comprising the steps of:
   obtaining values of a plurality of factors indicative of different patient health parameters, the plurality of factors comprising at least a plurality of blood chemistry test results;
   operatively associating the values of the plurality of factors with a unique identifier for the patient in a database;
   calculating a Z-score for each of the plurality of factors using at least one processing device;
   converting absolute values for each Z-score into a scaled value representative of the statistical significance of the plurality of factors using the at least one processing device for displaying, on the display device, a radar graph depicting the scaled value of the scaled value of the Z-scores for the plurality of factors,
   generating the radar graph to define at least a plurality of arcuate sections, said arcuate sections representing identified ones of the plurality of factors;
   wherein the scaled value of the Z-scores are plotted in at least one of the arcuate sections such that a magnitude of the scaled value of the Z-score from a center of the radar graph indicates a deviation from a normal range.

2. The method for presenting patient test data on a display device according to claim 1, further comprising the steps of:
   adjacently grouping, in the radar graph, Z-scores for related ones of the plurality of factors.

3. The method for presenting patient test data on a display device according to claim 2, wherein the act of adjacently grouping, in the radar graph, Z-scores for related ones of the plurality of factors comprises grouping together any one or more of Z-scores for CKD, CR, BUN or K relating to kidney function.

4. The method for presenting patient test data on a display device according to claim 2, wherein the act of adjacently grouping, in the radar graph, Z-scores for related ones of the plurality of factors comprises grouping together any one or more of Z-scores for ALB, A1 C, GLC, or BMI relating to diabetes.

5. The method for presenting patient test data on a display device according to claim 2, wherein the act of adjacently grouping, in the radar graph, Z-scores for related ones of the plurality of factors comprises grouping together any one or more of Z-scores for AlkP, ALT, Bil, or AST relating to liver function.

6. The method for presenting patient test data on a display device according to claim 1, wherein Z-scores of differing magnitudes are highlighted in correspondence with a magnitude of the Z-score.

7. The method for presenting patient test data on a display device according to claim 1, wherein a highlighting of each arcuate section is determined by a position of the arcuate section relative to the center point of the radar graph.

8. The method for presenting patient test data on a display device according to claim 1, wherein Z-scores having log values less than about 1.0 are displayed via one or more arcuate sections having a first form of highlighting, wherein Z-scores having log values between 1.1 and 2.5 are displayed via one or more arcuate sections having a second form of highlighting different than the first form of highlighting, and wherein Z-scores having log values greater than 2.5 are displayed via one or more arcuate sections having a third form of highlighting different than the first and second forms of highlighting.

9. The method for presenting patient test data on a display device according to claim 1, wherein the act of obtaining values of a plurality of factors indicative of different patient health parameters comprises obtaining values of a plurality of factors indicative of different patient health parameters on a plurality of different dates.

10. The method for presenting patient test data on a display device according to claim 1, wherein the display device is disposed remotely from at least one of a physical computer-readable medium bearing the database and the at least one processing device.

11. The method for presenting patient test data on a display device according to claim 1, wherein the radar graph defines at arc that is greater than 90 degrees.

12. The method for presenting patient test data on a display device according to claim 1, wherein the radar graph defines at arc that is greater than 180 degrees.

13. The method for presenting patient test data on a display device according to claim 1, wherein the radar graph defines at arc that is equal to or less than 360 degrees.

14. The method for presenting patient test data on a display device according to claim 1, wherein the radar graph is user-customizable to display user-selected ones of the plurality of factors.

15. A system for displaying patient test data comprising: a computer comprising at least one processor operable to:
   obtain values of a plurality of factors indicative of different patient health parameters, the plurality of factors comprising at least a plurality of blood chemistry test results;
   determine a Z-score for each of the plurality of factors;
   convert absolute values for each Z-score into scaled values; and
   display a radar graph depicting the Z-scores for the plurality of factors, the radar graph subdivided into a plurality of arcuate sections,
   wherein the scaled values are plotted from a center point of the radar graph, with the Z-scores of identified ones of the plurality of factors being representing as highlighted arcuate sections extending from the center point of the radar graph outwardly in correspondence with a magnitude of each Z-score such that the higher magnitude of the scaled value of each representative Z-score indicates a higher deviation from a normal range.

* * * * *